US007569341B2

(12) United States Patent
Niemeyer et al.

(10) Patent No.: US 7,569,341 B2
(45) Date of Patent: Aug. 4, 2009

(54) NUCLEIC ACID DIRECTED IMMOBILIZATION ARRAYS AND METHODS OF ASSEMBLY

(75) Inventors: Christof M. Niemeyer, Bremen (DE); Charles R. Cantor, Del Mar, CA (US); Takeshi Sano, Boston, MA (US); Cassandra L. Smith, Boston, MA (US)

(73) Assignee: Trustees of Boston University, Boston, MA (US)

( * ) Notice: Subject to any disclaimer, the term of this patent is extended or adjusted under 35 U.S.C. 154(b) by 0 days.

(21) Appl. No.: 08/967,269

(22) Filed: Nov. 7, 1997

(65) Prior Publication Data
US 2003/0118595 A1 Jun. 26, 2003

Related U.S. Application Data

(63) Continuation of application No. 08/530,912, filed on Sep. 20, 1995, now abandoned, which is a continuation-in-part of application No. 08/189,448, filed on Jan. 31, 1994, now Pat. No. 5,561,043.

(51) Int. Cl.
*C12Q 1/68* (2006.01)
(52) U.S. Cl. ........................................................ 435/6
(58) Field of Classification Search .................. 435/6, 435/7.1, 7.2, 810, 9; 436/501; 536/22.1, 536/23.1, 24.1, 24.3–24.33, 25.3; 935/77, 935/78
See application file for complete search history.

(56) References Cited

U.S. PATENT DOCUMENTS

| 4,478,914 | A |   | 10/1984 | Giese | 428/407 |
|---|---|---|---|---|---|
| 4,676,980 | A |   | 6/1987 | Segal et al. | 424/85 |
| 4,711,955 | A | * | 12/1987 | Ward et al. | 536/29 |
| 4,775,619 | A | * | 10/1988 | Urdea | 435/6 |
| 4,925,785 | A |   | 5/1990 | Wang et al. | 435/6 |
| 5,124,246 | A |   | 6/1992 | Urdea et al. | 435/6 |
| 5,177,000 | A |   | 1/1993 | Bazinet et al. | 435/7.23 |
| 5,273,882 | A |   | 12/1993 | Snitman et al. | 435/6 |
| 5,338,532 | A |   | 8/1994 | Tomalia et al. | 424/1.49 |
| 5,437,977 | A |   | 8/1995 | Segev | 435/6 |
| 5,474,911 | A | * | 12/1995 | Pontius | 435/41 |
| 5,556,748 | A | * | 9/1996 | Douglas | 435/6 |
| 5,561,043 | A | * | 10/1996 | Cantor et al. | 435/6 |
| 5,648,213 | A | * | 7/1997 | Reddy et al. | 435/6 |
| 5,747,254 | A | * | 5/1998 | Pontius | 435/6 |

FOREIGN PATENT DOCUMENTS

GB  WO 89/10977  * 11/1989

OTHER PUBLICATIONS

Matthews et al. (1988) Analytical Biochemistry, vol. 169, pp. 1-25.*
Matthews et al., Analytical Biochemistry, vol. 169, pp. 1-25, 1988.*
Dunn et al., Cell, vol. 12, pp. 23-36 (1977).*

Bos et al. "In Vitro Evaluation of DNA-DNA Hybridization as a Two-Step Approach in Radioimmunotherapy of Cancer," Cancer Research (1994) vol. 54, pp. 3479-3486.*
Tautz et al. "A Non-Radioactive in situ Hybridization Method for the Localization of Specific RNAs in Drosophila Embryos Reveals Translational Control of the Segmentation Gene hunchback," Chromosoma (1989) vol. 98, pp. 81-85.*
Fahrlander et al., "Amplifying DNA Probe Signals: A 'Christmas Tree' Approach," *Bio/Technology*, vol. 6, pp. 1165-1168, Oct. 1998.
Ito et al., "Affinity Capture Electrophoresis for Sequence-Specific DNA Purification," *GATA*, 9(3): 96-99, 1992.
Ito et al., "Sequence-specific DNA purification by triplex affinity capture," *Proc. Natl. Acad. Sci. USA*, vol. 89, pp. 495-498, Jan. 1992.
Ruzicka et al., "Immuno-PCR with a Commercially Available Avidin System," *Science*, vol. 260, pp. 698-699, Apr. 1993.
Murray et al., "Atomic force microscopy of biochemically tagged DNA," *Proc. Natl. Acad. Sci. USA*, pp. 3811-3814, May 1993.
Green, "Avidin and Streptavidin", In: Wilcheck, M. & Bayer, E.A. etd., Method in Enzymology, vol. 184. San Diego; Academic Press, 1991, pp. 51-67.
Klevan et al., "Biotinylated Nucleotides for Labeling and Detecing DNA" In: Wilcheck, M &Bayer, E.A., Method in Enzymologym, vol. 184, pp. 561-577, San Diego: Academic Press 1991.
Argarana et al., "Molecular cloning and nucleotide sequence of the streptavidin gene", Nucleic Acids Research, vol. 14, No. 4, 1986, pp. 1871-1882.
Sano et al., "A streptavidin-Protein a Chimera that Allows one-step Production of a Variety of Specific antibody Conjugates", Bio/Technology, vol. 9, Dec. 1991, pp. 1378-1381.
Sano et al., "Expression of a cloned streptavidin gene in *Escherichia coli*", Proc. Natl. Acad. Sci., vol. 87, pp. 142-146, Jan. 1990.
Cram, "The design of Molecular Hosts, Guests, and Their Complexes", Angewandte Chemie, vol. 27, No. 8, Aug. 1988, pp. 1009-1112.
Chetverin et al., "Oligonucleotide Arrays: New Concepts and Possibilities", Bio/Technology, vol. 12, Nov. 1994, pp. 1093-1099.
Fodor et al., "Light-Directed, Spatially Addressable parallel Chemical Synthesis", Research Article, Feb. 1991, pp. 767-773.

(Continued)

*Primary Examiner*—Jerry Lin
(74) *Attorney, Agent, or Firm*—Nixon Peabody LLP

(57) ABSTRACT

The invention relates to supramolecular bioconjugates and to methods for assembling and utilizing supramolecular bioconjugates. Supramolecular bioconjugates comprise a plurality of first nucleic acids and a plurality of mediators wherein each mediator comprises a second nucleic acid complementary to a sequence within said plurality of first nucleic acids. To assemble a supramolecular bioconjugate, one or more sets of bioreactive agents are coupled to the plurality of mediators, forming a plurality of bioreactive complexes The plurality of bioreactive complexes are hybridized to the plurality of first nucleic acids to form the supramolecular bioconjugate. Bioconjugates can be used to detect and isolate targets, to screen samples for targets such as antigens, to treat patients with multiple agents or to diagnose disorders in the form of a kit.

20 Claims, 7 Drawing Sheets

OTHER PUBLICATIONS

Pease et al., "Light-generated oligonucleotide arrays for rapid DNA sequence analysis", Proc. Natl. Acad. Sci., vol. 91, pp. 5022-5026, May 1994, pp. 5022-5026.

Lehn, "Perspectives in Supramolecular Chemistry—From Molecular Recognition towards Molecular Information Processing and Self-Organization", Angew. Chem. Int. Ed. Engl. vol. 29 (1990) pp. 1304-1319.

Lehn, "Supramolecular Chemistry: Receptors, Catalysts, and Carriers", Science, vol. 227, No. 4689, Feb. 1985, pp. 849-856.

Niemeyer et al., "Oligonucleotide-directed self-assembly of proteins: semisynthetic DNA—...", Nucleic Acids Research, vol. 22, No. 25, (1994), pp. 5530-5539.

Lehn, "Supramolecular chemistry-Scope and Perspectives Molecules, Supermolecules, and Molecular Devices", Angew. Chem. Int. Ed. Engl. vol. 27, (1988), pp. 89-112.

* cited by examiner

NUCLEIC ACID DIRECTED IMMOBILIZATION ARRAYS AND METHODS OF ASSEMBLY

REFERENCE TO RELATED APPLICATIONS

This application is a continuation under 35 U.S.C. § 120 patent application Ser. No. 08/530,912, filed on Sep. 20, 1995, now abandoned, which claims the benefit of and is a continuation-in-part of application Ser. No. 08/189,448, filed on Jan. 31, 1994, now U.S. Pat. No. 5,561,043.

BACKGROUND

1. Field of the Invention

This invention relates to supramolecules comprised of bioreactive conjugates, and to bioconjugates that bind to bioreactive molecules with a high affinity and regioselectivity. The invention also relates to arrays of bioreactive supramolecules formed from bioconjugates and to methods for their assembly,

2. Background of the Invention

Supramolecular chemistry or chemistry beyond the molecule, involves the arrangement of molecules bound via non-covalent interactions to form supramolecules (Lehn, Angew. Chem. Int. Edn. English 29:1304, 1990) Although the individual components are important for determining the specific nature of a supramolecular structure, the super structure allows for functionality not achievable with the isolated components. The classic supramolecules which emphasize this basic principle are nucleic acids and some polypeptides, which are endlessly produced by living organisms.

Methods for assembling supramolecular compounds are under investigation for use as detection systems and for new material properties (Vogtle, *Supramolecular Chemistry*, Wiley, Chichester, UK, 1991; Schneider et al., eds., *Frontiers in Molecular Organic Chemistry and Photochemistry*, VCH Publishers, Weinheim, Germany 1991). The development of supramolecular systems using combined functionalities of individual molecules is stimulated by natural models. Cells, as the ultimate molecular machines, use ensembles of proteins, nucleic acids and other macromolecules to perform complicated tasks such as replication, transcription and translation. Natural recognition systems such as receptor binding and nucleic acid hybridization enable biological systems to perform complex functions. One example of the unique functionality of supramolecules in nature is the machinery of photosynthesis. This complex of proteins and other biochemicals contains the supramolecular structure of the thylakoid membrane of chloroplasts (Bassi et al., Eur. J. Biochem. 204:317-26, 1991). Some of the better characterized multi-subunit supramolecular biomolecules in nature are listed in Table 1.

TABLE 1

Supramolecular Bioconjugates in Nature

| Origin | Protein Conjugate | Mol. Wt. | No. of Subunits |
|---|---|---|---|
| Human | α-Crystallin | 810 kDa | 30* |
| Pig | Lipoate Succinyl Transferase | 1,000 kDa | 24* |
| Cirraformia | Erythrocruorin | 3,000 kDa | 162 |
| Bovine | Dihydrolipoyl Transacetylase | 3,120 kDa | 60 |
| *E. coli* | Pyruvate Dehydrogenase Complex | 4,600 kDa | 24 |
| Phage | FII Protein | 3,620 kDa | 180 |
| Cow Pea Chlorotic | Mottle Virus | 4,608 kDa | 180 |
| Chicken | Acetyl CoA Carboxylase | 4-10,000 kDa | |
| Potato Virus | X Protein | 35,000 kDa | 650 |
| Tobacco Mosaic Virus | | 40,000 kDa | 2130 |

*= approximate

The highly specific functionality of single supramolecular biological compounds like *E. coli* pyruvate dehydrogenase complex, with 24 subunits and a molecular weight of 4 to 5 million is well recognized and utilized for numerous applications in biological and medical fields. However, little has been reported about synthetic combinations of naturally occurring molecules or their modified analogs to make supramolecular constructs with new and possibly enhanced, properties (Kabanov et al., Protein Engng. 4:1009-18, 1991).

The lack of uniform conjugation techniques and the long duration of current synthesis procedures serve as substantial barrels to regioselective supramolecular construction. Simple heterodimeric assemblies can be prepared by chemical cross linking (Wong, *Chemistry of Protein Conjugation and Cross-linking*, CRC Press, Boca Raton, Fla., 1991), but it is not always possible or economically feasible to cross-link the enormous variety of functional macromolecules available. Each macromolecule requires a special tailored procedure for cross linking. A uniform chemical conjugation procedure suitable for a wide variety of chemicals has not been developed. Furthermore, most bioreactive molecules have limited stability and would not endure long multiple step synthesis without losing their bioreactive properties. Limited chemical stability has discouraged the employment of successive conjugation strategies for the synthesis of supramolecular bioreactive constructs comprising labile moieties. The desire to limit the exposure of bioreactive subunits to inactivating conditions and to simplify or decrease the number of manipulative steps during supramolecular assembly have not been addressed by current technology.

Recombinant technology has been successfully employed for conjugating different regions of proteins not normally found adjacent in nature. While such technology is powerful, it is also limited to the biosynthetic capability of the host organism and subject to the limits of current technology. One limitation of recombinant DNA technology is the inability to synthesize non-proteinaceous compounds. In vivo expression place a weight limit of about 200 kilodaltons on recombinant proteins. Expression is limited to those proteins which are not toxic when expressed ill high levels in vivo. Proteins which are acidic, basic, hydrophobic or hydrophilic, may all be toxic and inexpressible at high levels.

There is a need for simplified methods for increasing both the regiospecificity and resolution, as well as reducing the cost of supramolecular compound construction. Improved methods which reduce cost, eliminate processing steps and minimize opportunities for inactivation and cross-contamination are highly desired but not addressed by current technology.

SUMMARY OF THE INVENTION

The present invention overcomes the problems and disadvantages associated with current strategies and designs and provides novel supramolecular bioconjugates and arrays, and methods for creating and using these conjugates and arrays.

One embodiment of the invention is directed to methods for assembling supramolecular bioconjugates comprising a plurality of first nucleic acids and a plurality of mediators wherein each mediator comprises a second nucleic acid complementary to a sequence within said plurality of first nucleic acids. The one or more sets of bioreactive agents are coupled to the plurality of mediators to form a plurality of bioreactive complexes and the plurality of bioreactive complexes are hybridized to the plurality of first nucleic acids to form the supramolecular bioconjugate. The nucleic acids of each plurality may contain a common nucleotide sequence or sets of different common sequences. Bioreactive agents may be antibodies, aptamers, lectins, antigens, cytokines or nucleic acids, or nearly any substance that can be screened or be used to screen samples For specific targets. Multiple bioreactive agents may also be used in sets to create arrays of agents. Each bioreactive agent may further comprise a binding agent such as avidin, streptavidin or biotin. Supramolecular bioconjugates may be used as assembled arrays or be further treated with, for example, enzymes or chemicals, to remove nucleic acid. Bioconjugates may also be attached via the first nucleic acid, the second nucleic acid or the mediator to a support such as a plastic or ceramic surface.

Another embodiment of the invention is directed to methods for assembling supramolecular bioconjugate comprising connecting a plurality of bioreactive agents to one or more sets of mediators to form a plurality of bioreactive targeting complexes. Each mediator comprises a targeting nucleic acid wherein a targeting sequence of the targeting nucleic acid is unique to the bioreactive agent of the complex. A plurality of positioning nucleic acids are provided, each containing at least one positioning sequence complementary to the targeting sequence, and hybridizing targeting sequences to positioning sequences to form a supramolecular bioconjugate. Positioning nucleic acids maybe attached, either covalently or non-covalently, to a support such as ceramic, plastic or metal.

Another embodiment of the invention is directed to methods for detecting a target antigen in a sample. A supramolecular bioconjugate comprised of a plurality of target antigen-specific antibodies is contacted to a sample suspected to contain the target antigen. Target antigen is detected from its association with one or more mediators of the bioconjugate. Target antigens which can be detected include antigens characteristic of disorders or harmful genetic variations such as an activated oncoprotein, a tumor antigen, a parasitic antigen, a bacterial antigen, a fungal antigen, a recombinant protein or a cytokine. Target antigens may be directly or indirectly labeled to aid in detection. Target detected may be further located and form a specific fingerprint on the supramolecular bioconjugate.

Another embodiment of the invention is directed to methods for treating disorders with supramolecular bioconjugates. The bioconjugate is created containing an antibody specific a harmful target antigen and coupled with a toxin. The bioconjugate is administered to the patient.

Another embodiment of the invention is directed to supramolecular bioconjugates. Supramolecular bioconjugates comprise a plurality of first nucleic acids, a plurality of second nucleic acids hybridized to the plurality of first nucleic acids and one or more sets of bioreactive agents non-covalently attached to the plurality of second nucleic acids. The supramolecular bioconjugate may be in solution or fixed to a solid support.

Another embodiment of the invention is directed to diagnostic kits comprising supramolecular bioconjugates. The supramolecular bioconjugate comprises a plurality of positioning nucleic acids attached to a solid support in a pre-determined pattern and a plurality of targeting nucleic acids hybridized to the positioning nucleic acids wherein each targeting nucleic acid is connected to a bioreactive agent forming a supramolecular bioconjugate containing a pre-determined array of bioreactive agents. The bioreactive agent may be an antibody, an aptamer, an antigen, a lectin, a cytokine, a toxin, a coupling agent, a protein, a nucleic acid, a recombinant protein or a combination thereof. Such diagnostic kits may be used, for example, for the detection of multiple pathogens or for the determination of cell types.

Another embodiment of the invention is directed to therapeutic compositions comprising supramolecular bioconjugates. The supramolecular bioconjugate comprises a plurality of positioning nucleic acids attached to a solid support in a pre-determined pattern and a plurality of targeting nucleic acids hybridized to the positioning nucleic acids wherein each targeting nucleic acid is connected to a bioreactive agent forming the supramolecular bioconjugate containing a pre-determined array of bioreactive agents. Examples of useful bioreactive agents include cytokines, cytotoxins, bacteriostaitic agents, bacteriocidal agents, antiparasitic agents, antiviral agents, antifungal agents and chemotherapeutic agents.

Other embodiments and advantages of the invention are set forth, in part, in the description which follows and, in part, will be obvious from this description and may be learned from practice of the invention.

DESCRIPTION OF THE INVENTION

Figure 1:
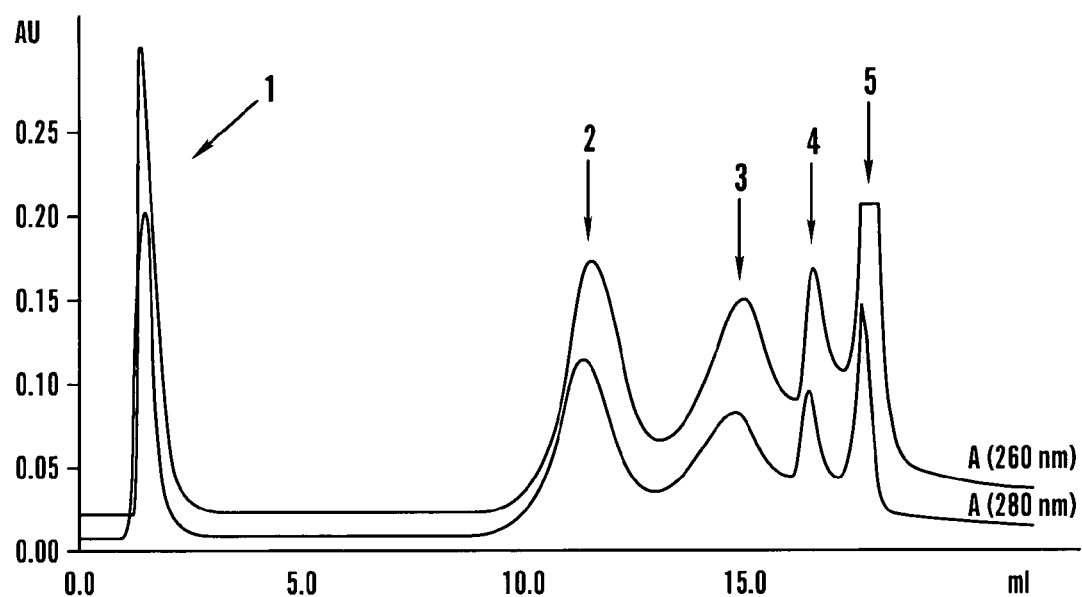
FIG. 1 Chromatogram of products from cross-linking reactions of streptavidin (STV) and thiolated DNA.

As embodied and broadly described herein the invention is directed to methods for constructing supramolecular bioconjugates, to supramolecular bioconjugates comprising arrays of bioreactive agents, and to methods for assembling supramolecular bioconjugates with enhanced selectivity and sensitivity.

A bioreactive conjugate is a covalent or non-covalent complex that uniquely associates a bioreactive agent with a particular targeting nucleic acid containing a particular targeting sequence. This targeting sequence, by hybridizing with a complementary positioning sequence of a positioning nucleic acid, can direct the associated bioreactive agent to a particular position in a supramolecular bioconjugate.

Supramolecular bioconjugates possess properties that can be attributed to the combination of components and also new properties, not previously known from the individual components. For example, a supramolecular bioconjugate comprising an array of polyspecific antibodies will have a specificity greater than the sum of the collection of individual antibodies alone. The synergistic combination of binding potentials of a supramolecular bioconjugate can mean the difference between binding and not binding a target. Properties such as strength and specificity will show cooperative effects not demonstrated when the components are individually considered. According to the invention, such properties would be expected from any supramolecular bioconjugate comprised of molecules which have a particular affinity for other molecules.

Supramolecular bioconjugate have encoded in their three dimensional structure, precise structure-function-mechanism relationships which can accelerate the rate of a particular function beyond that of the individual components. For example, a supramolecule bioconjugate which is an enzyme may have, in addition to the active sites and catalytic groups, subunits which bind substrate, stabilize the transient intermediate, recruit co-factors and release product. The combined rate of the supramolecular enzyme, which can simultaneously proximate multiple functional groups on a substrate and stabilize transient intermediates, exceed the individual sequential unimolecular or bimolecular reactions of the individual functional groups themselves.

Methods for the assembly of supramolecular bioconjugate arrays using nucleic acid-containing bioreactive conjugates offers significant advantages. One principal advantage is that assembly can be tightly controlled and regulated. For example, using direct sequential conjugation, supramolecules can be assembled in a highly orderly state. However, this method is still easily modified by adding, substituting or deleting components or by altering the order which the components are added together. For example, labile moieties may be protected with protection groups until additive assembly is complete. Protection groups are removed in a final step to activate the array. Other benefits include reduced degradation of bioreactivity and minimal costs while also providing necessary regioselectivity for the assembly of supramolecular bioreactive arrays. Regioselectivity and regiospecificity refer to a process that favors the purposeful, and position specific assembly of a macromolecule or an array of macromolecules. Regioselectivity may be stringent wherein a single spacial arrangement is favored or, alternatively, relaxed wherein a plurality of spacial arrangements are favored. The single assembly step, requiring minimal handling time, is suited for supramolecular construction when the individual bioreactive agents are labile. Oligonucleotide-directed assembly can be used for the construction of macromolecular assemblies, supramolecules or nano-structures with, in principle, no limitations on the nature and number of their constituents.

As embodied and broadly described herein, the invention comprises constructs, compositions and methods for the non-enzymatic accumulation of products at specific sites in vivo or in vitro. Antibody and oligonucleotide specificities may be combined to greatly amplify the accumulation of functional moieties at the site or sites of a disorder in vivo, or the detection of a disorder or other contaminant in vivo or in vitro. Supramolecular bioconjugates, possessing an almost limitless amount of functional activity, are assembled where needed and, at the same time, with minimal nonspecific accumulations in normal tissues. The diseased-to-normal tissue ratios of supramolecular constructs is very high for both diagnostic and therapeutic applications. In addition, multimeric nucleic acid constructs can be used to create 3-dimensional assemblies of nucleic acid based polymers.

A preferred embodiment of the invention is directed to a construct comprising a streptavidin molecule to which is coupled to a single-stranded nucleic acid.

This approach has a number of advantages. As streptavidin has a high affinity for biotin, nucleic acids coupled to the streptavidin molecule are strongly and specifically bound to biotinylated macromolecules of various descriptions.

Constructing Regiospecific Supramolecular Arrays

One embodiment of the invention provides methods for efficiently assembling arrays of bioreactive molecules into a supramolecular bioconjugate. These methods are based upon the surprising discovery that bioreactive agents conjugated to single-stranded nucleic acids can assemble regioselectively in a single step to form bioreactive arrays. Such supramolecular bioconjugates may be assembled by a number of methods. One method is to regioselectively place nucleic acids on a substrate to form a scaffold and hybridize bioreactive macromolecules connected to complementary nucleic acids onto this scaffold. Hybridizations may be simultaneous or sequential with steps which, using multiple sets of different bioreactive molecules, linearly or exponentially assemble the construct.

Another method is to produce a set of multivalent multi-specific subunits which can regioselectively self assemble into a supramolecular structure. A distinguishing characteristic of self assembling subunits is that the subunits comprise multiple, specific conjugatable moieties in a defined spacial arrangement which contact each subunit. The structure of the supramolecular product is determined by the structure and combination of the subunits. Many specific conjugatable moieties with high fidelity and avidity may be used including, for example, antibodies, lectins, antigens, cell surface receptors, nucleic acid binding proteins, avidin, streptavidin, biotin, cell adhesion molecules and nucleic acids. Conjugatable moieties may also be aptamers, natural or synthetic nucleic acid containing molecules that specifically bind to other molecules. Aptamers, due to sequence and three-dimensional structure, energetically favor one or more stable or flexible three dimensional shapes which specifically bind to a host of both small and large molecular weight ligands. Furthermore, once bound, an aptamer may assume a different conformation which, as desired, may strengthen or weaken binding.

Self assembling subunits, because of their unique spacial and combinatorial arrangement of conjugatable moieties, permits only certain supramolecular arrangements. These supramolecular structures will assemble either in vitro or in vivo from their component subunits into predetermined structures with or without external support. Furthermore, supramolecular bioconjugates may be assembled from multiple self-assembled supramolecular subunits or from a plurality of unassembled elements in a single step.

This one step assembly method can form bioreactive macromolecular arrays comprising very large numbers of individual elements. A useful number of individual elements in the positioning array may range from about one to ten, to one hundred, to one thousand or to tens of thousands or greater, depending on the intended use of the supramolecular bioreactive array. In assembling arrays or in specific uses, it may be useful to generate arrays with elements in the range of ten thousand, a hundred thousand, or a million or more elements. Preferably, the number of elements is in the range of about $10^1$ to about $10^{12}$ and, more preferably, in the range of about $10^2$ to about $10^{10}$, although greater and smaller numbers are sometimes desired depending on the particular application. The resultant array may be used directly or it may be separated to form multiple useful subarrays. Each assembled array may comprise individual unique elements, common elements or a combination of common and unique elements.

Another embodiment of the invention is directed to a method for making a nucleic acid-containing polymer comprising the steps of creating a monomer comprised of a streptavidin molecule attached to one or more single-stranded nucleic acids. In a typical example, bioreactive agents are initially biotinylated and may be archived. When needed, sets of bioreactive conjugates, each comprising a different nucleic acid for regioselective assembly, are constructed by contacting the archived biotinylated macromolecule with a mediator containing a nucleic acid coupled to streptavidin to form a bioreactive conjugate. A support is provided which is a supramolecular template containing a set of single-stranded nucleic acid segments that specify the eventual location of the bioreactive conjugates referred to as the positioning nucleic acid sequences. The set of bioreactive conjugates is contacted to the support comprising an ordered assembly of distinct or different single-stranded nucleic acid regions where each single-stranded region in the support is complementary to a particular targeting nucleic acid sequence in one member of the set of bioreactive conjugates. The mixture of bioreactive conjugates and the support are placed in conditions that favor the annealing of complementary nucleic acids. The sequences of the nucleic acids enable the bioreactive conjugates to assemble purposefully and regioselectively on the support to form an array of supramolecular bioreactive agents. The order in which the bioreactive conjugates are placed in the array may allow synergistic and complementary interaction or cooperation among its individual members.

The elements of the supramolecular array includes supports containing a template made up of an array of single-stranded positioning nucleic acid segments, and bioreactive conjugates containing both single-stranded targeting nucleic acid segments which have sequences complementary to the positioning nucleic acid segments and bioreactive agents uniquely associated with particular targeting sequences. The targeting nucleic acid and the bioreactive agent in the bioreactive conjugate may be covalently coupled, either directly or through intermediates. Alternatively, the targeting nucleic acid may be non-covalently coupled to the bioreactive agent in bioreactive conjugates which contain a mediator. Mediators comprise a targeting nucleic acid coupled to one member of a specific binding pair where the other member of the pair is coupled to the bioreactive group. These elements are described in more detail below.

Supports

In the assembly of arrays of bioreactive molecules, a support is provided which contains an ordered array of positioning nucleic acids which constitutes the template. Supports may be one dimensional, two dimensional or three dimensional. As such, supports may also be microscopic, submicroscopic or macroscopic. Supports may comprise a variety of materials such as nucleic acids, proteins, hydrogels, beads, membranes, filters, plastics, glasses, ceramics, metals, wood or cellulose or combinations of these materials. Preferably, the support is a hybridization chip.

The sequence of each of the nucleic acid species, including the first, second, third or more species, may be the same or different, may comprise a small or large number of complementary sequences, may have a defined sequence or may contain. random or variable sequences. In the simplest case, a long single-stranded nucleic acid, synthesized in vitro or purified from organisms may be used as a one-dimensional support. The supporting nucleic acid may have a plurality of single-stranded regions for hybridization to bioreactive conjugates. Alternatively, single-stranded nucleic acids may be cross-linked to hydrogels such as acrylamide and agarose to form a two-dimensional or three-dimensional supports. Supports may be of many different shapes such as circles, plates or beads. Beads may comprise materials normally used to for chromatography beads including agarose, acrylamide, cellulose, sepharose and other natural or synthetic polymers. For example, the surface of a bead may be coated with nucleic acid for hybridization or other materials such as polymer-coated magnetic beads, and metals (e.g. magnetic beads). A hydrogel with a loose structure allowing relatively free flow of bioreactive agents may be used as a three-dimensional support. A support may also comprise solid or porous surfaces made from materials such as membranes, filters, metals, plastics, cellulose or combinations of such materials. Multiple two-dimensional supports may be stacked on top of one another to form a three-dimensional support, Alternatively, a three-dimensional support may be constructed with substantially porous material or permeable material for supramolecular arrays. Each element of the array comprises one or more nucleic acids having a positioning sequence for hybridization to bioreactive conjugates. The sequences of nucleic acids in different elements may be either the same or different depending on the use of the array. For example, an array may he used in a bioassay of agents in which it is desirable to place a positive control agent adjacent to each test agent. A plurality of elements may contain the same nucleic acids for the attachment of the positive control agent. In other situations, a plurality of elements may contain different nucleic acids for the attachment of different test agents.

Another embodiment of the invention is directed to nucleic acid-containing polymers formed from monomers comprising a streptavidin molecule bound to one or more biotinylated single-stranded nucleic acids. Functional groups of the support may be attached to the monomers at the streptavidin molecule or the nucleic acid, may be a portion of the nucleic acids themselves or may be added after assembly of the polymer. Polymers may be a solid, a liquid or a gel. Useful solids include membranes, plastics, coatings, resins and other materials of defined porosity including chromatography reagents (which may also be a gel), pharmaceuticals, and nearly any substance with can be assembled from monomers. Useful liquids include polymeric substances such as plastics and coatings which may be paints, dyes, metals and other inorganic and organic compounds. Polymers can also be utilize in nanotechnology in the design and construction of microcircuits and electronic switches, in manufacturing of continuous protein fibers such as silk and in the production of multi-layered micro-components.

Nucleic acids for the positioning sequences, as well as target sequences, may be made synthetically, recombinantly or isolated from biological sources using techniques known to those of ordinary skill. Nucleic acids covalently attached to biotin may be purchased commercially or created through recombinant or biochemical techniques. Biotin can be obtained commercially or purified as the water-soluble vitamin. Streptavidin is a protein composed of four identical subunits with an approximate molecular weight of 60,000 daltons and can be purchased commercially or purified from *Streptomyces avidinii* (N. M. Green, Biochem. J. 89:585-89, 1963). Streptavidin is preferred, but avidin may also be utilized in these constructs with nearly equal efficiency, and the use of the term streptavidin herein is intended to include avidin as a substitute.

Nucleic acids to be used in supramolecular arrays may be obtained from natural or synthetic sources. Synthetic nucleic acid may be synthesized using an automatic oligonucleotide synthesizer. Naturally occurring primers may be isolated from biological or recombinant sources, using processes such as restriction endonuclease treatment and denaturation. The nucleic acid may comprise DNA, RNA or PNA (polyamide-nucleic acid or another such analog). In some applications where the digestion of the nucleic acid may be desirable after the assembly of the supramolecular bioreactive array, use of an easily digestible nucleic acids such as RNA may be desired. In other applications where the supramolecular bioreactive array may be used with the nucleic acid attached, the use of a more digestion-resistant species of nucleic acid such as DNA may be preferred. The support may be charged and that charge may be adjusted using highly charged nucleic acid species, such as DNA or RNA, or uncharged nucleic acids such as polyamide nucleic acids (PNA).

Mediator

Another embodiment of the invention is directed to a novel bioconjugates useful in the assembly of supramolecular bioreactive arrays. One function of a supramolecular bioconjugate is to allow the rapid conjugation of a bioreactive agent to a nucleic acid. Useful supramolecular bioconjugates may also comprise, for example, a nucleotide oligomer attached to a protein which shows high avidity. Such proteins include streptavidin, antibodies, aptamers, lectins, nucleic acid binding proteins and cell adhesion molecules.

The supramolecular bioconjugate nay be formed by chemically cross-liking a nucleic acid to streptavidin or another appropriate member of a specific binding pair. The member of the specific binding pair may be selected from the group consisting of avidin, streptavidin, biotin, protein A, antibodies, aptamers, antigens, nucleic acid binding proteins and cell adhesion molecules. Appropriate proteins, including streptavidin, may be derivatized with excess sulfosuccinimidyl 4[p-maleimidophenyl] butyrate. The derivatized protein is contacted with deprotected thiolated oligonucleotide at room temperature to form a bioconjugate for use in preparing supramolecular compounds. The resultant product may be purified, for example, by ion-exchange chromatography.

Target nucleic acid constructs may comprise one, two or three species of single-stranded nucleic acids bound to streptavidin or a greater plurality of bound nucleic acids forming, for example, a structure comprising a streptavidin core from which multiple nucleic acids emanate such as dendritic starbursts. Generally, starbursts have between about 4 to about 20 emanating nucleic acids, typically between 5-15 and more typically probably between 6-12 nucleic acids. These nucleic acids may be the same or different may comprise complementary sets of sequences. Nucleic acids may comprise a double-stranded portion when, for example, a particular structure is desired for the assembled network of constructs or to facilitate coupling of one or more functional groups. In addition, specific nucleotide sequences may be engineered into one or more of the nucleic acid species to attract a particular pharmaceutically active component to the site of aggregate formation after formation has been completed. Multiple different sequences can be introduced to allow for the administration of different pharmaceutical components.

Nucleic acid species may comprise DNA, RNA or PNA, although it may be possible to substitute short sequences of amino acids for a part of the nucleic acid. Nucleic acid is typically about 10 to about 600 nucleotides in length, preferably about 15, 20, 25, 30, 35, 40, 45, 50, 55, 60, 65 or 70 nucleotides in length, and more preferably between about 20 to about 60 nucleotides in length. Although larger nucleic acid species may be used, longer sequences are generally not preferred because larger nucleic acids tend to have unacceptable melting temperatures and steric hinderance effects.

Another embodiment of the invention is directed to a general class of multimeric constructs comprising a coupling agent to which is attached two or more single-stranded nucleic acids. Coupling agents are chemicals which allow for the attachment of multiple species of nucleic acid. Some of the more useful agents include streptavidin, avidin, succinimidyl 4-(N-maleimidomethyl)cyclohexane-1-carboxylate (SMCC), 5'-amino-containing oligonucleotides, 5'-thiol-containing oligonucleotides and polyamidoamines. These chemicals can be used to create multimeric nucleic acid constructs containing 2, 3, 4, 5, 6, 7 or more species of nucleic acids per molecule. Resulting aggregates will have multiple points of interaction. Constructs may further contain the same functional groups as described above and those functional groups may be the nucleic acids themselves.

In a preferred embodiment, supramolecular bioconjugates comprise streptavidin-conjugated oligonucleotides. One advantage of streptavidin is the extreme chemical and thermal stability and conjugate avidity of the protein (Sano et al., 258:120-22, 1992). The tetrameric protein streptavidin binds the small water-soluble molecule biotin (vitamin H) rapidly and with extraordinary specificity. Since many biotinylated materials are commercially available or can be prepared with a variety of mild biotinylation procedures, biotin-streptavidin conjugates form the basis of many diagnostic and analytical tests. Covalent attachment of an oligonucleotide moiety may provide streptavidin with a specific binding domain for complementary nucleic acids in addition to its four native binding sites for biotin. This bispecificity of the hybrid molecules allow them to serve as selective and efficient connectors in oligonucleotide-directed self-assembly of, for example, proteins and other bioreactive agents.

The streptavidin molecule may be bound with one, two, three or more nucleic acid species. Three is preferred to provide the maximum number of functional groups or supporting structures while still providing a free biotin binding site on the streptavidin molecule for further binding which may also be to a functional group. Star burst arrangements are also possible with multivalent linkers which radiate 4, 5, 6, 8, 10, 12 or more single-strand species. Starburst dendrimers may be constructed with a divalent linker such as SMCC (succinimidyl 4-(N-maleimidomethyl) cyclohexane-1-carboxylate) and a derivatized amino- or thiol-containing compound such as reduced S-pyridylcysteamine modified oligonucleotide. These linkers have 6-12 available amines for binding nucleic acids. Other similar approaches may be used which start with easily prepared 5'-amino- or 5'-thiol-containing oligonucleotides.

Bioreactive Agents

A bioreactive agent is a moiety with biological activity that provides the appropriate function when present in the desired position in a supramolecule established by the positioning nucleic acid/targeting nucleic acid pair with which the agent is associated. A functional group attached to the nucleic acid multimer provides the functionality desired in the bioreactive agent. Functional groups are those portions of the construct which provide functional or structural activity directed toward the specific use of the construct. Examples of functional groups include radioisotopes, stable isotopes, toxins, cytokines, pharmaceutically active moieties or components, proteins, metals, metabolic analogs, genes, aptamers, antigens, lectins, enzymes, antibodies and antibody fragments, nucleic acids, oxidizing agents, bacteriostatic and bacteriocidal agents, or combinations or parts thereof. The bioreactive agent may be selected from the group consisting of antibodies, lectins, antigens, cytokines, nucleic acids, metals, metabolites, metabolic analogs, enzymes, cofactors, bacteriostatic agents, bacteriocidal agents, amino acids, peptides, protein, chemotherapeutic agents, avidin, streptavidin, biotin, toxins, cytotoxic agents, substrates, antiviral agents, antifungal agents monosaccharides, polysaccharides and combinations and fragments thereof. Bioreactive agents may also be aptamers, nucleic acid binding molecules that are specific for a particular target which may be nearly any molecule or substance.

Nucleic acids may be bound with functional groups such as, for example, saccharides, lipids, fatty acids, nucleic acids, metals and amino acids. These conjugate polymers form as and can be formed into products such as solids, liquids and gels. Alternatively, a part or portion of the nucleic acid species may itself be the functional group. For example, certain nucleotide sequences are known binding sites for specific proteins. A nucleic sequence can be engineered into the species to be bound to streptavidin and the resulting construct utilized.

Functional groups which may be useful for the treatment of disorders in a patient include radio isotopes, stable isotopes, toxins, cytokines, pharmaceutically active moieties, proteins, metals, metabolic analogs, genes, antigens, enzymes, antibodies and antibody fragments, nucleic acids, oxidizing agents, antibiotics, chemotherapeutic agents, bacteriostatic and bacteriocidal agents, and combinations and parts thereof. For example, radioisotopes are useful against certain neoplasias. Toxins such as animal toxins, plant toxins, bacterial toxins, fungal toxins, viral toxins and parasitic toxins, are useful against specific infections. Preferred toxins include *Pseudomonas* toxins, *Diphtheria* toxins, *Escherichia* toxins and ricin. Cytokines are useful when targeted to certain cells or tissues to elicit a desired function attributed to that cytokine. Useful cytokines include T cell growth factors, B cell growth factors, granulocyte/macrophage growth factors, granulocyte growth factor, macrophage growth factor, stem cell growth factor, transforming growth factor, erythropoietin, bone morphogenic proteins, differentiating agents, interleukins, interferons, hormones, components of the complement system and combinations thereof. Particular antigens may also be useful when targeted to diseased cells or tissues to induce or bolster an immune response. Functional groups which are proteins may be coupled to other proteins either covalently, such as fusion proteins or chimeric proteins, or non-covalently such as electrostatically. These other proteins may be proteins which recognize and bind to specific sequences present only on the nucleic acid species of the constructs. In this way, pharmaceuticals can be delivered to multiple sites within a patient simultaneously and with a great deal of specificity and accuracy.

A series of bioreactive agents, useful in a bioreactive array, may be biotinylated and stored until needed. Biotinylation reagents are commercially available for targeting a variety of functional groups, including primary amines, sulfhydryls, carboxyls, carbohydrates, tyrosines, histidines, guanidines and cytosines. Bioreactive agents may also be derivatized to place functional groups on their surface. Storage of biotinylated agents is preferably performed by a method which preserves the bioreactive function of the agents. Such conditions are known for the specific agent or can be determined by routine investigation. Storage of individually aliquoted vials of bioreactive agents in liquid nitrogen is; suitable for most bioreactive reagents.

Attachment of functional groups may be non-covalent such as by electrostatic, hydrophobic or hydrophilic interactions, or by covalent binding. Techniques for attaching functional groups to the multimer are particular to the group being attached and may be direct or indirect. For example, direct attachment may be by covalent modification of the functional group, the nucleic acid or both. There are also many different chemical coupling agents such as streptavidin, avidin, SMCC, 5'-amino-containing oligonucleotides, 5'-thiol-containing oligonucleotides and polyamidoamines. Indirect attachment may be by modification of the functional group, the nucleic acids or both with another substance such as *E. coli* or other single-stranded or double-stranded binding proteins such as Rec A proteins, T4 gene 32 proteins or major or minor groove nucleic acid binding proteins, and G protein complexes. Coupling agents which facilitate attachment are preferably specific binding pairs such as avidin/biotin, aptamer/target, streptavidin/biotin, receptor-ligand interactions, antibody/antigen pairs, *Staphylococcus aureus* protein A/IgG antibody Fc fragment, and chimeras including streptavidin/protein A chimeras.

Methods for the production of antigen-specific antibodies are well known to those of ordinary skill and some are disclosed in *Current Protocols in Immunology* (J. E. Coligan et al., eds.; John Wiley and Sons; New York, N.Y., 1991), and *Antibodies: A Laboratory Manual* (E. Harlow and D. Lane, eds.; Cold Spring Harbor Press; Cold Spring Harbor, N.Y., 1988). Antibodies may be of the classes IgG, IgM, IgA, IgE, IgD and parts and combinations thereof, and may be monoclonal or polyclonal, or comprise fragments of antibodies such as Fab fragments or Fv fragments. Antibodies or fragments may be connected to targeting nucleic acids using the same reactions as taught for streptavidin. Alternatively, antibodies may be coupled to biotin and bound to streptavidin-nucleic acid mediators. Biotin conjugated antibodies may be obtained commercially or prepared from purified biotin and the desired antibodies. Techniques for the coupling of biotin to antibodies are well known to those of ordinary skill and some are disclosed in *Immunochemical Protocols* (Methods in Molecular Biology, vol. 10; M. M, Manson, ed.; Humana Press; Totowa, N.J., 1992). Other bioreactive molecules may be connected to targeting nucleic acids by similar reactions.

Another embodiment of the invention is directed to the rapid synthesis of oligonucleotide-conjugated bioreactive agents. A plurality of oligonucleotides with different sequences may be coupled to a bioconjugate such as streptavidin, avidin or biotin. These coupled oligonucleotides may be stored until needed. Storage may be performed by freezing or refrigeration with or without preservatives, stabilizers, buffers and antioxidants. When a bioreactive agent conjugated to an oligonucleotide is needed, the appropriate aliquots of both are removed from storage and connected. In the case when the bioreactive agent is biotinylated and the oligonucleotide is attached to streptavidin, conjugation may occur at room temperature, merely by combining the two reagents in a single container.

Assembly or Supramolecular Arrays

Assembly of the supramolecular bioconjugate is performed by hybridizing the targeting nucleic acid on a bioconjugate containing a bioreactive agent with the positioning nucleic acid on the support. The complementary nature of the single-stranded nucleic acids causes the array to assembly simultaneously in solution. The hybridization potential of nucleic acids may be controlled by adjusting the length, the sequence and the hybridization conditions. A one-to-one correspondence between the bioreactive agents and positions may be used to ensure a unique bioreactive agent attaches to each position in the supramolecular array. The number of bioreactive agents may be greater than the available positions such that more than one species of bioreactive agents are affixed to each position. It is also useful in some applications to place one bioreactive agent into multiple positions on a support. In those instances the number of species of bioreactive agents is less than the number of positions on the support.

The length of the optimal oligonucleotide depends on many factors, including the sequences attached to the solid support, the source of the nucleic add such as DNA, RNA or PNA, the nucleotide composition such as GC content and the composition of the hybridization reaction. Generally the optimal length of the oligonucleotide attached to the bioreactive macromolecule or attached to the support may be from about 5 to about 600 bases in size. More preferably, the nucleic acid may be between about 20 to about 60 bases in length. In the case where the nucleic acid is the support, the nucleic acid is usually between about 10 and about 1000 bases in length and preferably between about 20 and about 60 bases in length.

The targeting nucleic acid and positioning nucleic acid will be substantially complementary under hybridization conditions. Substantially complementary refers to two regions of nucleic acid with a sufficient number of bases on both regions enabling two regions to hybridize. Two nucleic acid regions may hybridize even if less than 100% of the bases are matched. While the method of this application works well if every base of the two regions of nucleic acids matches, the method also works if a few mismatches exist between the first nucleic acid region and the second nucleic acid region. Mismatched complementary regions may be useful for the attachment of a single conjugate to multiple regions on a support.

Hybridization of single-stranded nucleic acids to form double-stranded nucleic acids depends on the length and composition of the primer as well as the concentration of salts, buffers and other chemicals. Hybridization utilizes the ability of a single-stranded DNA, RNA or PNA to anneal to a sequence which is substantially complementary even in the presence of unrelated nucleic acids. Hybridization conditions may be adjusted to different stringencies to change the proportion of complementarily in the nucleotide sequence required for annealing. Relaxed hybridization condition may be useful for placing one bioreactive agent on a number of sites. Stringent conditions may be used to ensure the proper location for each bioreactive macromolecule. A number of chemicals known to affect the strength of the nucleic acid double bond are listed in Table 2.

TABLE 2

Chemicals That Affect Nucleic Acid Binding and Non-Specific Binding

| | |
|---|---|
| Formamide | Sodium Chloride |
| Dried Milk | Sodium Dodecyl Sulfate |
| Sodium Citrate | Sodium Phosphate |
| Tetramethylammonium Chloride | Non Specific Genomic DNA |
| Tetraethylammonium Chloride | Other Salts |

These chemicals may be used to adjust the hybridization conditions to suit the bioreactive macromolecules involved. For example, if a bioreactive molecule is sensitive to heat, formamide may be used to reduce hybridization efficiency and dextran sulfate may be used to reduce hybridization time. Other chemicals may be used to reduce the nonspecific binding of bioreactive macromolecules directly to the support. Such chemicals usually belong to the group of detergents such as SDS, tween, triton X-100. To further reduce background, nonspecific binders such as milk proteins, serum proteins and serum albumin may be added to nonspecifically block binding sites on the support.

Submicroscopic Supramolecules

One embodiment of the invention is directed to methods for making nucleic acid-containing polymers formed from monomers of multimeric nucleic acid constructs. Polymers can be targeted with biotin-conjugated antibodies and formed in vivo or in vitro. Constructs can also self-assemble to form useful products. Because the base monomer comprises mostly nucleic acid, it may be desirable to eliminate that nucleic acid after the aggregate has assembled. Nucleic acid can be degraded and removed with enzymes such as specific or nonspecific nucleases or alkali treatments followed by one or more washings with a buffer.

Macroscopic Arrays of Supramolecular Bioconjugates

The assembly of supramolecular bioreactive arrays of this embodiment comprises a hybridization step between a targeting nucleic acid attached to the bioreactive agent and a positioning nucleic acid attached to a solid support, such as a nitrocellulose membrane or a plastic plate. In particular, different positioning sequences can be attached to discrete areas of such a support, and addition of bioconjugate with targeting sequences can produce a solid support having bioreactive agents in discrete positions forming a spatially defined array of bioreactive agents. Such arrays may be free in a solution or attached to a solid support and, for example, further treated with enzymes of chemicals such as sodium hydroxide to degrade the nucleic acids and transfer the array of bioreactive agents to the support.

Diagnostic Uses of Supramolecular Conjugates

Another embodiment of the invention is directed to diagnostic aids and methods for using diagnostic aids for the in vitro detection of a target in a sample. Diagnostic methods comprise the addition of conjugated antibody and labeled constructs to the sample to detect the presence or location of a specified target. The diagnostic aid usually comprises a biotinylated antibody specific for the target and a multimeric nucleic acid construct labeled with a detectable label. The biotin-conjugated antibody may be polyclonal or monoclonal or antibody fragments such as Fab or Fv fragments. Constructs may comprise one, two, three or more nucleic acid species attached to the streptavidin molecule. Nucleotide sequences may be the same or different, and preferably, the constructs are prepared in complementary sets to be administered sequentially. The detectable label may be a radioisotope, stable isotope, enzyme, fluorescent or luminescent chemical, chromatic chemical, metal or electrical charge. Each of these labels can be detected through various means known to those of ordinary skill such as by autoradiography, nuclear magnetic resonance (NMR), magnetic resonance imaging (MRI) and other suitable detection means.

The target may be a protein, nucleic acid, metal, cytokine, viral or bacterial component, immunoglobulin, enzyme or a part or combination thereof. Targets may also be contaminants in the environment or other harmful substances that are suspected of having accumulated in the patient. The are virtually no limits to the types of targets which can be detected provided that they can be identified antigenically or by hybridization kinetics. As multiple elements or multiple constructs can be accumulated at a target site, targets undetectable by other means including polymerase chain reaction (PCR), can be detected with multimeric constructs and in many instances, immediately detected visually, a significant advantage over current methodologies including PCR procedures. The basic techniques of PCR are described in U.S. Pat. No. 4,683,195, and variations thereof described in U.S. Pat. Nos. 5,043,272, 5,057,410 and 5,106,727.

Another embodiment of the invention is directed to in vitro methods for detecting a target in a sample. For example, one method comprises the steps of conjugating an antibody specific for the target with biotin and adding the conjugated antibody to the sample. A multimeric nucleic acid construct is prepared comprising one or more biotinylated single-stranded nucleic acids bound to streptavidin. The construct is labeled with a detectable label and the labeled construct added to the sample. Examples of detectable labels include radio isotopes, stable isotopes, enzymes, fluorescent and luminescent chemicals, chromatic chemicals, metals mid electrical charges. Alternatively, the biotinylated antibody may be combined with streptavidin coupled to a particular nucleic acid before addition to the sample. After the antibody-nucleic acid conjugate is added to the sample, bound antibody can be detected by the addition of a label connected to a complementary nucleic acid.

Labeled constructs may be added once or many times to facilitate accumulation of label at the target site and subsequent detection of the target. Targets which can be detected include proteins, nucleic acids, metals, cytokines, viral and bacterial components, immunoglobulins, enzymes and parts and combinations thereof. Labeled constructs may be detected and localized in the sample using, for example, autoradiography, visual detectors, fluorescent detectors, radioactivity detectors, chromatic detectors, electrical detectors and any other means suitable for the particular label chosen.

When testing biological samples for target substances, the presence or absence of target may be indicative of a disorder. Samples for testing may be obtained from tissues, cells, blood, urine, cerebrospinal fluid, lymph and amniotic specimens. For example, amniotic cells can be tested for genetic disorders. Numerous cancers can be confirmed by the presence of tumor-associated antigens in samples of blood or urine. The presence of a viral infection can be confirmed by the presence of viral specific antibodies or sometimes antigen in a sample of the patient's serum. Disorders which can be detected by this method include diseases, infections, neoplasias and genetic defects and deficiencies. Samples from environmental sources, such as lakes, streams, rivers, land-fills, marshes and just plain earth, may be used to detect certain contaminants such as metals, pesticides, microorganisms or toxic wastes. Samples obtained from manufacturing processes of raw materials, intermediate or finished product may be tested for the presence or absence of certain targets including contaminants. Alternatively, sample may be tested to determine the concentration of various ingredients in the finished product as a means for quality control.

Another embodiment of the invention is directed to methods for detecting a disorder in a patient in viva. Antibody, which may be polyclonal or monoclonal, is conjugated with biotin and administered to the patient. A multimeric nucleic acid construct comprising one or more biotinylated single-stranded nucleic acids bound to streptavidin is labeled with a detectable label. Useful labels include radio isotopes, stable isotopes, enzymes, fluorescent and luminescent chemicals, chromatic chemicals, metals and electrical charges. Labeled constructs are administered to the patient and their location determined by autoradiography, NMR, MRI or other means suitable for the label. Disorders which can be detected include diseases, infections, neoplasias and genetic defects and deficiencies. Diagnosis of the particular disorder may be for precise targeting of other therapeutic procedures such as surgical or radiotherapy, or as a means for determining the presence or severity of the disorder.

Therapeutic Uses of Supramolecular Conjugates

Another embodiment of the invention is directed to methods for treating a disorder comprising the steps of administering a nucleic acid-conjugated antibody specific for the disorder and a second nucleic acid construct to the patient. The second nucleic acid constructs may contain functional groups such as toxins, isotopes, antibodies or pharmaceutically active components directed against the disorder. The sequence of each of the two nucleic acid species is complementary so that the functional group is specifically directed to the nucleic acid-conjugated antibody. A sequence can be chosen that is unique and not present elsewhere in the patient's genome. One feature of non-identical sequence constructs is that when used for the treatment of patients, multiple treatments can be administered, repeatedly exposing the patient to the same collection of nucleic acids without the risk of an adverse immune response to the sequence. Biological side reactions from the added nucleic acid sequences would not be expected to occur.

Nucleic acids utilized may be complementary providing a further binding function to each construct. Complementary constructs can be used sequentially to maximize accumulation at a target site. Cycles of complementary constructs can be administered to create the aggregate in stages. In this manner, layered aggregates can be created using complementary constricts with distinct functional groups.

Another embodiment of the invention is directed to compositions comprising nucleic acid constructs plus a pharmaceutically acceptable carrier such as water, saline, alcohol, polyethylene glycol, oil, polysaccharides, salts, glycerol, stabilizers, buffers, anti-oxidants, emulsifiers and combinations thereof. The function of the carrier is to provide a suitable medium for introduction of the construct in or on the patient's body. When compositions are used internally, carriers of saline, buffer and salts maybe useful. When used externally, carriers such as water, oils and alcohols may be useful Compositions may further comprise other ingredients such as anti-oxidants to prevent oxidation of constructs, anti-bacterial or anti-viral agents to reduce contamination, or other chemotherapeutic agents to treat the disorder.

Another embodiment of the invention is directed to a method for treating a disorder in a patient comprising the steps of administering an antibody, specific for the disorder, and a multimeric nucleic acid construct to the patient. The supramolecular bioconjugate may comprise antibodies against antigens specific for a disorder such as a disease, a tumor, a genetic variation or a combination thereof. In particular embodiments, the antibody is specific for tumor antigens, viral antigens or parasite antigens. The antibody may be specific for activated oncogenes such as activated oncoproteins antigens selected from the group consisting of Myc, Gli, Mas, Met, Neu, Ras, Trk, Onc, Thy, Bcl, Tcl, Evi, Int, Mlvi, Erb, Src, Raf, Jun, Fos, Pim, Glv, Gin, Fis Lck, Dsi, Fim, Ahi, Mis, Spi and combinations thereof. Attached to the constructs are one or more functional groups to treat or prevent the specific disorder. Functional groups may be added before or after creation of the resulting aggregate of constructs. Functional groups may be attached to the streptavidin coupling agent via one or more of the nucleic acids. Multiple functional groups can be attached to a single construct and, if desired, constructs can be entirely saturated.

After assembly of the aggregate of constructs, the binding protein, which may be modified with another constituent thereby creating a chimeric or fusion protein product, is added to the assembly. In this manner, formation of the assembly can precede treatment. In addition, the old constituent can be removed and substituted with new constituents without disassembling the aggregate. Aggregates would be useful for many such substitutions. Further, because the aggregate is a biological substance, it is not harmful to a patient when used in, for example, therapeutic procedures. The aggregate is expected to persist in the patient's body for a sufficient period of time, possible days, weeks, months or longer, to complete a full course for most types of therapy.

Disorders in which constructs and compositions may be used for therapeutic or prophylactic purposes including diseases, infections, neoplasias and genetic defects and deficiencies. Neoplasias treatable in this manner include leukemias, lymphomas, sarcomas, carcinomas, neural cell tumors, squamous cell carcinomas, germ cell tumors, metastases, undifferentiated tumors, seminomas, melanomas, neuroblastomas, mixed cell tumors, neoplasias caused by infectious agents and other malignancies. Treatable infections include infections caused by bacteria, viruses and parasites, and also fungal infections such as yeast and deep fungal infections which are difficult to treat conventionally.

Preferably, complementary sets of nucleic acid constructs are prepared and sequentially administered. For example, a first set of identical constructs are administered and allowed to assemble. Next, a second set of complementary constructs are administered which bind and hybridize to the first set. This pattern or cycle is repeated as desired allowing the resulting assembly to build exponentially to a predetermined and possibly very large size. Alternatively, both sets of complementary construct may be mixed simultaneously provided the assembly has time to form. Assembly times are dependant upon the size of the individual constructs and the size of the assembly desired. Relatively short incubation periods of only seconds or minutes will be needed due to the rapid binding of biotin to streptavidin and rapid hybridization of complementary nucleic acids. Further, aggregates can be constructed at multiple sites even when those sites have not been previously identified. Defined structures can be created at specific sites and the activity of the functional groups attached to each construct will be concentrated at these sites, such as radioactivity at tumor sites or sites of metastatic spread of diseased cells.

Treatments may be administered topically to treat or prevent diseases and infections on the exterior of the patient, or administered parenterally, sublingually, rectally or enterally, to treat or prevent systemic disorders. Patients which may be treated with these methods include animals and preferably humans. Treatments, such as the treatment of neoplasias, may be supplemented with one or more chemotherapeutic agents such as alkylating agents, purines and pyrimidine analogs, vinca and vinca-like alkaloids, etoposides and etoposide-like drugs, antibiotics, corticosteroids, nitrosoureas, antimetabolites, platinum based cytotoxic drugs, hormonal antagonists, anti-androgens and anti-estrogens. Treatments may also be supplemented with other therapies such as radiation therapy or immune therapy to further attack the disorder.

The following experiments are offered to illustrate embodiments of the invention, and should not be viewed as limiting the scope of the invention,

EXAMPLES

Example 1

Synthesis of Nucleic Acids

The electrophilic addition of thiols to maleimides yielding stable thioester conjugates was chosen as the crosslinking reaction for the conjugation of streptavidin to nucleic acids. Oligonucleotides were purchased (Operon Technologies; Alameda, Calif.) and used without further purification. Thiolated oligonucleotides were purchased and delivered with a disulfide protection group (5'-PGS), which was removed by incubating 6 mM of oligonucleotide with 15 mM DTT dissolved in PBE (phosphate-buffered EDTA; 100 mM phosphate buffer, pH 6.8, 5 mM EDTA) at 37° C. for one hour. After deprotection the disulfide protection group was removed by gel filtration chromatography with a Sephadex G-25 column, NAP-10 columns (Pharmacia Biotech; Piscataway, N.J.).

The oligonucleotides synthesized are listed in Table 3.

TABLE 3

Oligonucleotide Sequences

| Name | Sequence | |
|---|---|---|
| UA | 5'-PGS-TCC TGT GTG AAA TTG TTA TCC GCT-3' | (SEQ ID NO 1) |
| TC-UA | 5'-PGS-AGC GGA TAA CAA TTT CAC ACA GGA-3' | (SEQ ID NO 2) |
| UB | 5'-PGS-GTA ATC ATG GTC ATA GCT GTT-3' | (SEQ ID NO 3) |
| BC-UB | 5'-B-ACC AGC TAT GAC CAT GAT TAC-3' | (SEQ ID NO 4) |
| TC-UB | 5'-PGS-AAC AGC TAT GAC CTC GAA TAC-3' | (SEQ ID NO 5) |
| UC | 5'-PGS-CCG GGT ACC GAG CTC GAA TTC-3' | (SEQ ID NO 6) |
| BC-UC | 5'-B-GAA TTC GAG CTC GGT ACC CGG-3' | (SEQ ID NO 7) |
| TC-UC | 5'-PGS-GAA TTC GAG CTC GGT ACC CGG-3' | (SEQ ID NO 8) |
| UD | 5'-PGS-CAG GTC GAC TCT AGA GGA TCC-3' | (SEQ ID NO 9) |

TABLE 3-continued

Oligonucleotide Sequences

| | | |
|---|---|---|
| UDX | 5'-PGS-CAG CTC GAC TCT AGA GGA TCC AGT GCC AAD CT-3' | (SEQ ID NO 10) |
| UE | 5'-PGS-AGT GCC AAG CTT GCA TGC CTG-3' | (SEQ ID NO 11) |

Primers for Carrier

| | | |
|---|---|---|
| BRSP-48 | 5'-B-AGC GGA TAA CAA TTT CAC ACA GGA-3' | (SEQ ID NO 12) |
| M13-1211 | 5'-GTA AAA CGA CGC CCA GT-3' | (SEQ ID NO 13) |
| M13-T7 | 5'-TCC TAA TAC GAC TCA CTA TAG CGG ATA ACA ATT TCA CAC AG-3' (T7 promoter underlined) | (SEQ ID NO 14) |
| HP | 5'-$^{32}$P-GCG GAT AAC AAT TTC ACA-3' Hybridization probe | (SEQ ID NO 15) |
| CHP | 5'-$^{32}$P-TGT GAA ATT GTT ATC CGC-3' Hybridization probe | (SEQ ID NO 16) |

PGS = thiolated
B = biotinylated

Five thiolated oligonucleotides, UA, UB, UC, UD and UE, each complementary to a portion of the 108 base region of the plus strand of M13mp18 DNA between a reverse sequencing primer hybridization site (#1233: New England Biolabs; Beverly, Mass.) and a universal 17 mer sequencing primer hybridization site (#1211; New England Biolabs; Beverly, Mass.) were utilized.

All biotinylated antibodies used were polyclonal rabbit IgG, purchased from Sigma Chem. Co. (St. Louis, Mo.); biotinylated rabbit anti-bovine IgG (#B-7140); biotinylated rabbit anti-dog IgG (#B-7640); biotinylated rabbit anti-mouse IgG (#B-8520). Alkaline phosphatase conjugated ,antibodies were also from Sigma (St. Louis, Mo.); rabbit anti-bovine IgG-alkaline phosphatase conjugate (#A-7914); rabbit anti-dog IgG-alkaline phosphatase conjugate (#A-6042); rabbit anti-mouse IgG-alkaline phosphatase conjugate (#A-2418). IgG antigens used were mouse IgG whole molecules (Pierce), bovine IgG whole molecules and dog IgG whole molecules (reagent grade, from Sigma Chem. Co.; St. Louis, Mo.).

Single-stranded DNA carrier was prepared by denaturing a polymerase chain reaction product. PCR was performed using a biotinylated plus strand primer (BRSP-48), a non-biotinylated minus strand primer (M13-1211) and M13mp18 DNA template (New England Biolabs; Beverly, Mass.). The resulting 123 bp fragment was desalted on a NAP-10 column and purified by ultrafiltration, 30,000 MW cut-off membrane (Amicon; Danvers, Mass.). Remaining primer contaminants were removed by ion exchange chromatography on a Mono Q HR 5/5 column by FPLC. The carrier was immobilized on streptavidin-coated magnetic microbeads (M-280; Dynal). Non-specific binding sites of the beads were blocked with Tris-buffered saline (TBS; 20 mM Tris-HCl, pH 7.3, 150 mM NaCl) supplemented with 0.5% non-fat dried milk powder, 5 mM EDTA and 1 mg/ml denatured herring sperm DNA (MESTBS) The immobilization step was carried out with a bead suspension (20 mg/ml) and biotinylated DNA (2-5 mM) in TEMN (10 mM Tris-HCl, pH 7.5, 1 mM EDTA, 1 M NaCl) for one hour at room temperature. After washing the beads with TEMN, the DNA duplex was denatured by resuspending the beads in 0.1 M NaOH (10 ml) for 10 minutes at room temperature. Removal of the supernatant was followed by washing with 0.1 M NaOH and then with biotin-saturated TBS supplemented with 0.05% Tween 20 and 5 mM EDTA (TETBS). Immobilized carrier was stored in TEMN at 4° C. The recovered single-stranded 123 base minus-strand DNA was analyzed by 12% denaturing polyacrylamide gel electrophoresis (PAGE).

RNA carrier was prepared by in vitro transcription using a 144 bp DNA as template. DNA template was prepared by PCR using M13-T7 and M13-1211 primers and purified by ion exchange chromatography. In vitro transcription was performed using T7 RNA polymerase. Unincorporated ribonucleoside triphosphates were removed using a spin column, Chroma Spin+TF-10 (Clontech Laboratories). Transcription efficiency was determined by non-denaturing PAGE in the presence of an excess complementary, $^{32}$P-labeled hybridization probe (CHP or M13-1211) with known specific activity (J. Sambrook et al., *Molecular Cloning: A Laboratory Manual,* 2nd Ed., Cold Spring Harbor Laboratory Press, Cold Spring Harbor, N.Y., 1989). Quantitation of the bands, using a PhosphorImager (Molecular Dynamics), gave typical efficiencies of 8-10 mol RNA/mol DNA template.

Example 2

Synthesis of Heterobifunctional Conjugate

Streptavidin (Boehringer Mannheim; Indianapolis, Ind.) was derivatized with excess sulfosuccinimidyl 4-[p-maleimidophenyl] butyrate (sulfo-SMPB; Pierce; Rockford, Ill.), a heterobispecific crosslinker, in a 600 ml reaction mixture, consisting of 3.8 mg/ml protein and 0.25 mg/ml sulfo-SMPB in PBS (100 mM K phosphate buffer, 7.3, 150 mM NaCl) to provide a maleimide functionality. After incubation for one hour at room temperature, products were desalted by ultrafiltration (30,000 MW cut-off membrane) and the buffer changed to PBE. Derivatized streptavidin (200 ml, 3.5 mg/ml in PBE) was mixed with 200 ml of a deprotected thiolated oligonucleotide (0.7 mM in PBE) at room temperature to yield a stable thioether-linked DNA-streptavidin conjugate. After 15 minutes and 30 minutes another 200 ml aliquot of the DNA solution was added. The mixture was incubated for an additional 30 minutes and excess DNA was removed by ultrafiltration (Centricon 30).

Crosslinked products were purified by ultrafiltration followed by ion exchange chromatography on a Mono Q HR 5/5 column by FPLC (Pharmacia Biotech; Piscataway, N.J.). Best results were achieved with the following run profile: 1 ml buffer A (20 mM Tris-HCl, pH 6.3, 0.3 M NaCl); sample injection; 4 ml buffer A, followed by a linear salt gradient of 22.6 mM/ml using buffer B (20 mM Tris-HCl, pH 6.3, 1 M NaCl); flow rate, 0.2 ml/minute. The elution profile of a typical purification is shown in FIG. 1. Peak fractions were collected, concentrated by ultrafiltration and stored in TBS at 4° C. for 3 months without noticeable degradation. $A_{260}$ and $A_{280}$ profiles of the eluate from the Mono Q column are listed in Table 4.

TABLE 4

Calculated $A_{260}/A_{280}$ Values for DNA-STV

| DNA/STV Ratio | Calculated $A_{260}/A_{280}$ |
|---|---|
| 1 | 1.05 |
| 2 | 1.27 |
| 3 | 1.40 |
| 4 | 1.49 |

Measured $A_{260}/A_{280}$ Ratios

| Peak Number | Observed (SD) | $A_{260}/A_{280}$ DNA/STV Ratio |
|---|---|---|
| 1 | 0.58 (0.03) | 0 |
| 2 | 1.03 (0.02) | 1.0 |
| 3 | 1.23 (0.07) | 1.9 |
| 4 | 1.42 (0.10) | 3.2 |
| 5 | 1.72 (0.10) | 11.7 |

Based on the $A_{260}/A_{280}$ profile, unconjugated streptavidin (peak 1) eluded first from the column and unconjugated DNA eluded as the fifth and last peak. Streptavidin molecules crosslinked to one, two or more nucleic acids eluded as the second, third and fourth peaks, respectively. The good conformity of the value for the nano-DNA adduct and the value for peak 2, the major product of the crosslinking reaction provided additional evidence that only a single species, namely the desired mono-DNA-STV hybrid, was present in this fraction.

Biotin binding of the purified hybrids was quantified by a chromatographic shift assay (R.-D. Wei, Methods Enzymnol. 18A:424-427, 1970). A ratio of 4.1 mole bound biotin/mole DNA-STV hybrid was observed. The result was in good agreement with the expected value of 4.0. DNA binding was investigated by gel-retardation experiments with a 5'-labeled complementary oligonucleotide as a probe. In the presence of the hybridization probe materials recovered from peak 2 showed a single band with a decreased mobility, whereas materials from peaks 3 and 4 gave complex band patterns, indicating the presence of multiple species. In control experiments, addition of non-complementary hybridization probes caused no band-shift.

A series of DNA-STV hybrid molecules with oligonucleotide moieties, of various sequences and lengths was prepared. When analyzed by PAGE, all results obtained indicated a 1:1 molar ratio of DNA to STY for the hybrid molecules present in ion exchange chromatography peak 2 (FIG. 1).

Figure 2:
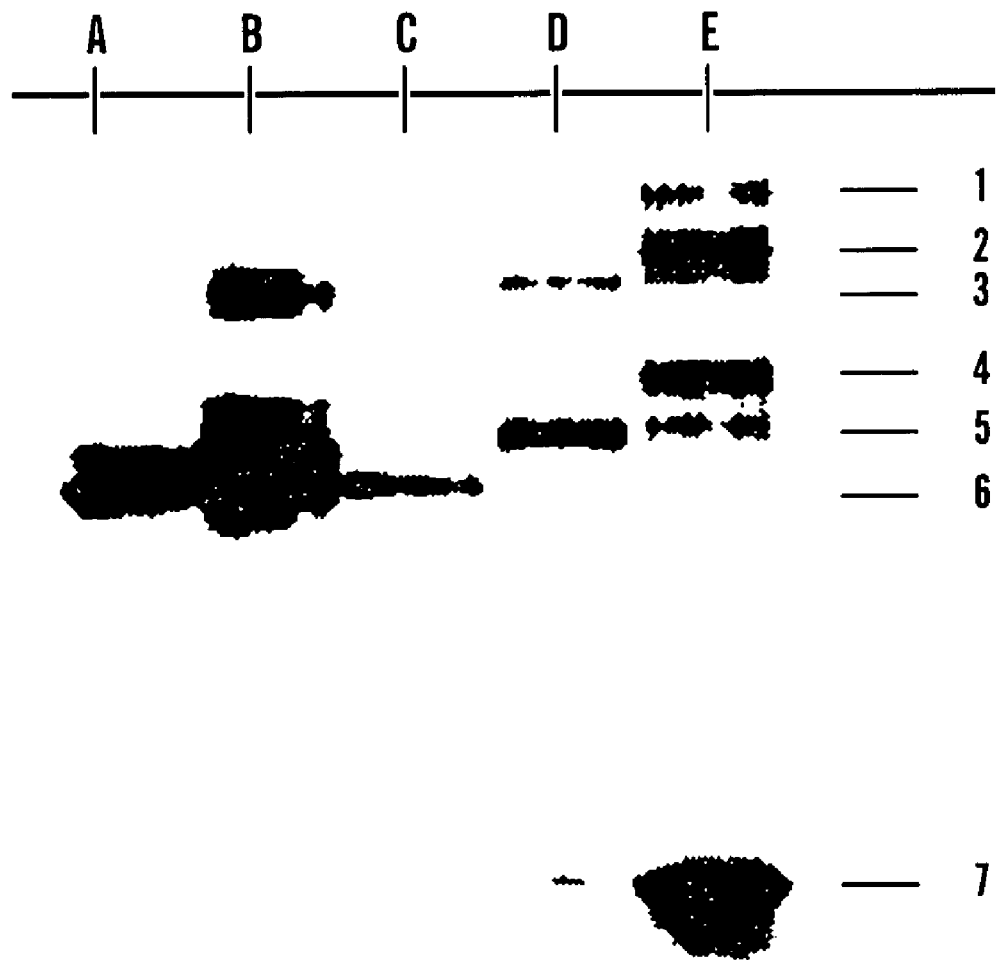
FIG. 2 Analysis of ion exchange chromatography peak fractions comprising one, two and three or more DNAs.

Fractions comprising the second, third and fourth peak were analyzed on a 8.5% non-denaturing polyacrylamide gel (FIG. 2). Two different concentrations of streptavidin-DNA were loaded on lanes A and B as controls and streptavidin-DNA migrated at position 6. Fraction 2 was loaded on lane C and migrated at position 6 as expected for streptavidin-DNA complexes. Fraction 3 was loaded on lane D and has a slower migration rate (position 5) due to an extra nucleic acid. Fraction 4 was loaded on lane E and shows a plurality of slower migrating bands corresponding to streptavidin with three or more nucleic acids attached.

Peak fractions from ion exchange chromatography were characterized by non-denaturing PAGE (FIG. 2). Peaks 2 gave a single band (lane C; position 6) co-migrating with a control sample containing mainly a mono-b-DNA-STV conjugate (lane A). In certain batches, small amounts of contaminants were observable as a slower migrating band. The main band resulting from peak 3 (lane D; position 5) co-migrated with a conventional di-b-DNA-STV conjugate, whereas peak 4 gave several, bands (lane E; positions 1-5) probably representing tri, tetra and higher DNA-contains species as well as free DNA (position 7).

Example 3

Synthesis ad Analysis of Biotinylated DNA-Streptavidin Conjugates

Control samples were prepared from streptavidin and the biotinylated oligonucleotide BRSP-48. Streptavidin (5 mg/ml; 900 pmol in 10 ml) was diluted with 20 ml of TE and 20 ml of a BRSP-48 solution (48 pmol/ml; 1.06 equivalents) were added. The mixture was incubated at room temperature on a shaker for 30 minutes. Similar mixtures were prepared containing the same final streptavidin concentration (1 mg/ml) with various biotinylated DNA concentrations, ranging from 4.7-144 pmol/ml (0.25-8 molar equivalents, respectively). Typically 5-8 ml of these solutions were mixed with 2 ml of a non-denaturing PAGE sample buffer and analyzed by gel electrophoresis.

Non-denaturing PAGE studies were performed on 8.5% polyacrylamide gels. Samples were applied as 5-15 ml portions containing 0.1-1 mg/ml protein (e.g. streptavidin 1.8-18 pmol/ml) in a sample buffer (final concentrations 20 mM Tris-HCl, pH 8.9, 7.5% glycerol, 0.002% bromophenol blue). Staining of the samples were performed with Coomassie Brilliant Blue (CBB), silver or ethidium bromide.

DNA binding was studied using a 5'-[$^{32}$P]-labeled 18 base oligonucleotide (HP) (58 pmol/ml, 260 cpm/pmol) as a probe, which is complementary to the UA sequence of the streptavidin-UA hybrid molecule. Various amounts of hybrid molecules (1-5 ml; 3.2-16 pmol) were mixed with 5 ml of the radiolabeled probe in an electrophoresis sample buffer. Samples were diluted with 10 mM Tris-HCl, pH 7.6, 1 mM EDTA to a final volume of 15 ml and subjected to non-denaturing PAGE. Analysis of the gel was conducted by autoradiography with a PhosphorImager. Additional gel-retardation experiments were conducted with UA-streptavidin and UB-DNA hybrids, using conventional streptavidin conjugates with biotinylated DNA (BRSP-48 and BC-UB) as a complementary probe.

Example 4

Assembly of a Heterodimeric Construct

Wells of a microtiter plate (Immulon-4; Dynatech) were coated with mouse, bovine or dog IgG (50 ml protein solution at a concentration of 20 ng/ml in 50 mM borate buffer, pH 9.5) for approximately 14 hours at room temperature.

Streptavidin (50 ng/ml) was immobilized under the same conditions. Plates were washed three times with TBS (200 ml each) and nonspecific binding sites were blocked with 100 ml MESTBS containing 0.02% NaN$_3$, followed by three TBS washes (200 ml each) Unless otherwise stated, the following incubation steps were carried out at room temperature. In a typical experiment, 2-5 pmol of a hybrid (1 mM in TBS) was mixed with 2-5 pmol biotinylated material (IgG or alkaline phosphatase, 1 mM in TBS) and incubated for 15-30 minutes at room temperature. Undesired cross-coupling between multiple-biotinylated molecules and free biotin-binding sites of the hybrids was avoided by quenching the reaction with TETBS (10 ml) saturated with free biotin. Preconjugated samples were diluted with a reagent dilution buffer (RDB; 9 parts TETBS and 1 part MESTBS) and applied to antigen-coated microtiter plates. After incubation, the plate was washed six times with TETBS (200 ml) and two times with TBS (200 ml) and alkaline phosphatase-dependent color reactions were carried out with the addition of 200 ml of 1 M diethanolamine, pH 9.8 and 0.5 mM $MgCl_2$ containing 10 mM p-nitrophenyl phosphate (pNPP). After incubation for 60 minutes at 37° C. the reaction was quenched by adding EDTA to a final concentration of 125 mM. Absorbance at 405 nm of a 50 ml aliquot was determined with an EIA-Reader.

Figure 3:
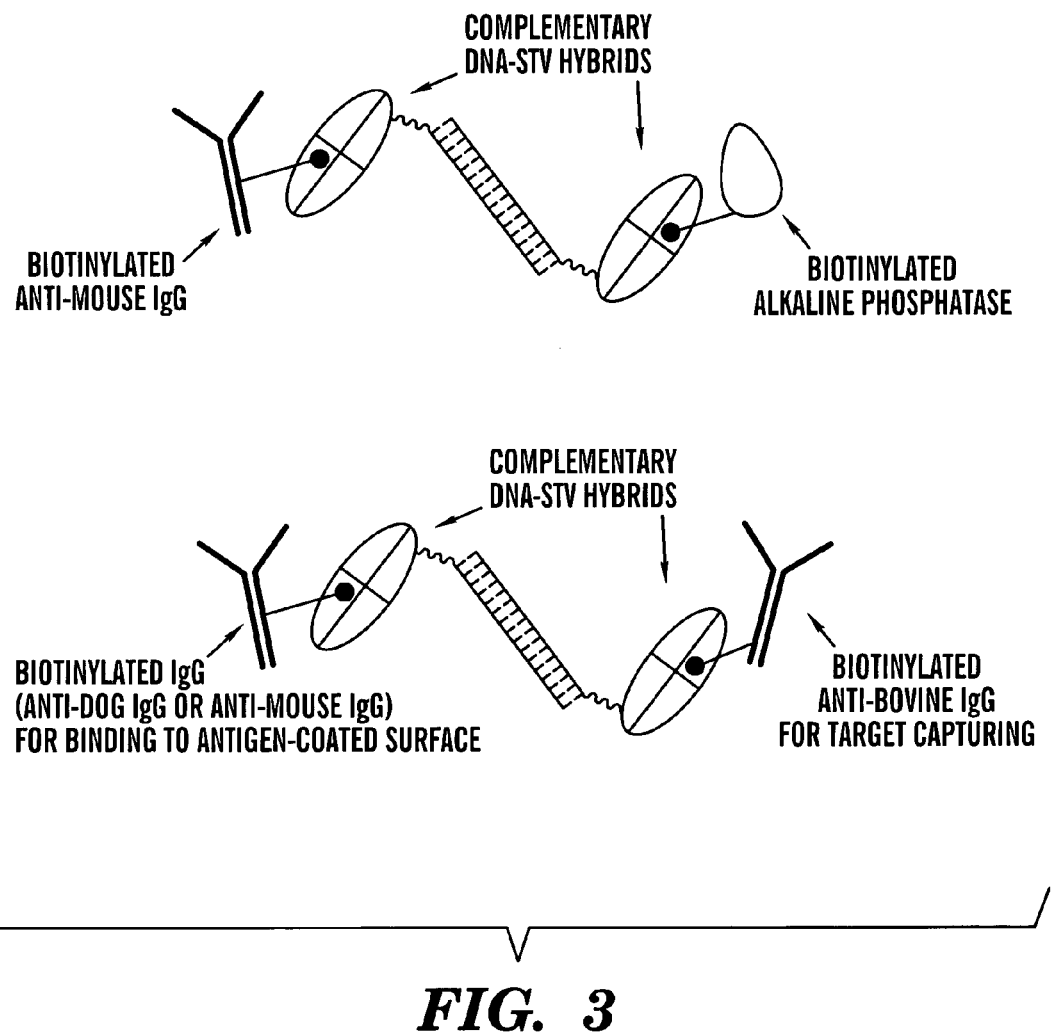
FIG. 3 Schematic representation of bifunctional constructs.

A bifunctional construct was constructed by self-assembly of two complementary DNA-STV hybrids, one preconjugated to biotinylated AP and the other to biotinylated anti-mouse IgG (FIG. 3). The TC-UA-streptavidin hybrid (4 pmol) was preconjugated with 4 pmol of biotinylated anti-mouse IgG. Control A was the T-C-UB-streptavidin hybrid; control B contained IgG only. Three solutions, diluted with biotin-saturated RDB to a final concentration of 0.2 mM, were mixed with an equimolar amount of a 50 nM solution prepared from UA-streptavidin hybrid and biotinylated alkaline phosphatase (4 pmol each), as described above. The mixture was diluted with RDB to a final putative supramolecular construct concentration of 5 nM (which corresponds to an IgG concentration of ~0.6 mg/ml). Microtiter plate, coated with mouse IgG or with dog IgG were used to test the binding capability and enzymatic activity of the bifunctional constructs. Five-fold serial dilutions of the reagent were applied to mouse IgG-coated microtiter plates which were then incubated for 2 hours. After washing, alkaline phosphatase-dependent color reactions were carried out as described above and the absorbance at 405 nm of a 100 ml aliquot was determined.

IgG bifunctional constructs were constructed by conjugating, in separate tubes, 4 pmol of TC-UA-streptavidin to 4 pmol of biotinylated anti-mouse IgG or biotinylated anti-dog IgG (samples A and C, respectively). Controls were prepared in parallel, lacking the DNA-streptavidin hybrid (samples B and D, respectively). In another tube, 16 pmol of the complementary hybrid (UA-streptavidin) was preconjugated to biotinylated anti-bovine IgG (16 pmol). All samples were diluted to final hybrid concentrations of 0.2 mM, Aliquots (10 ml) of the anti-bovine conjugate were mixed with the same amount of samples A-D and the mixtures were subsequently diluted with RDB to a final hybrid concentration of 8 nM. Five-fold serial dilutions were prepared and 50 ml of each of these solutions was applied to a microtiter plate, previously coated with mouse IgG and dog IgG antigen. The plate was incubated for 2 hours and washed three times with TBS (200 ml each). Incubation with bovine IgG (50 ml of a 0.8 mg/ml solution in RDB) was performed to allow the immobilized construct to capture antigens. After washing with two times with TBS (200 ml each) and three times with TETBS (200 ml each), successful assembly and capture were tested by a 1 hour incubation with an anti-bovine IgG-alkaline phosphatase conjugate (50 ml of a 0.65 U/ml solution in RDB) and a subsequent alkaline phosphatase (pNPP) reaction. The absorbance reading obtained from the pNPP reaction indicated the functionality of both tethered ends.

Two control experiments, one with a DNA-STV-IgG conjugate with non-complementary sequence (control A) and the other in which the DNA-STV-AP conjugate was incubated with the biotinylated TgG only (control B) were carried out.

Figure 4:
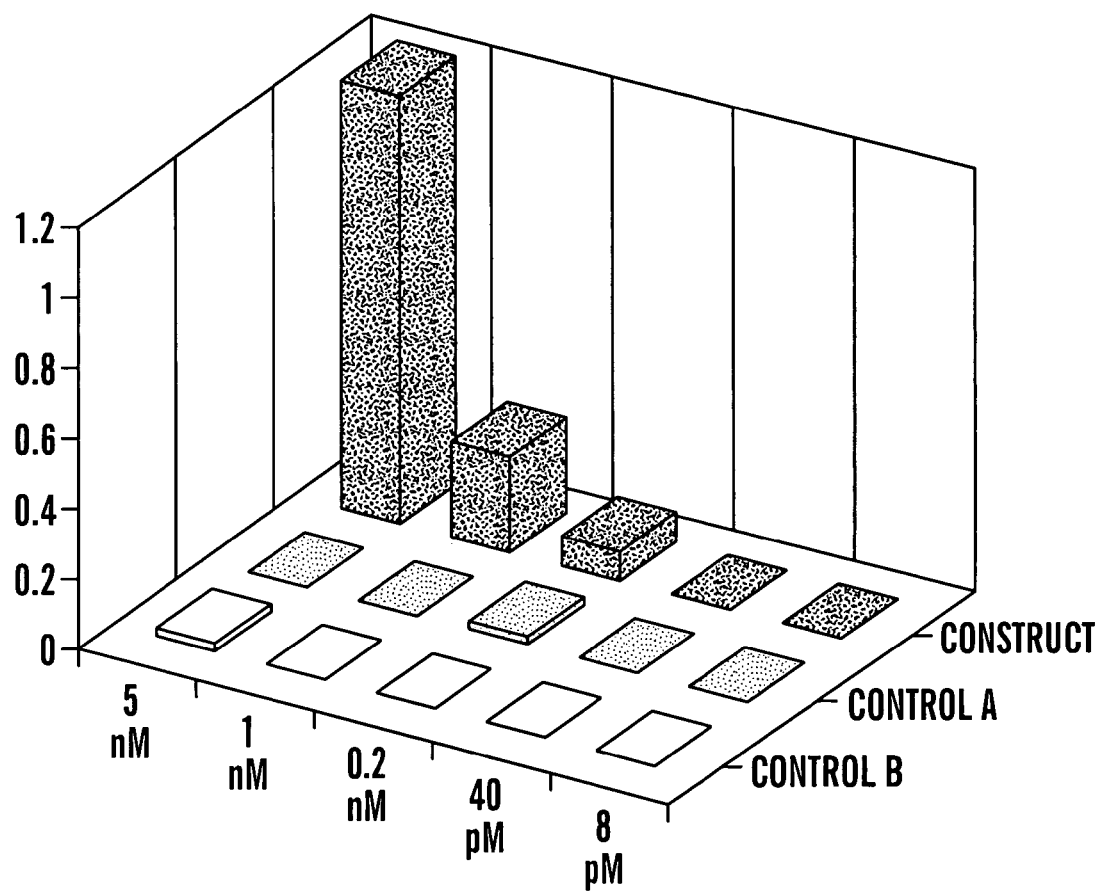
FIG. 4 Demonstration of the bifunctionality of the antibody.

As shown in FIG. 4, a signal was obtained only when the two complementary DNA-tagged components were present. From absorbance measurements at 405 nm, the signal-to-noise ratio was greater than 60 at a reagent concentration of 6 μg/ml for the controls and 1.42 and 3.46 for the antimouse and antidog bispecific constructs respectively. Results obtained in control experiments with no functional bispecific construct present suggested the relatively high backgrounds, especially in the case of immobilized mouse IgG, are primarily due to non-specific binding of the polyclonal antibodies.

Example 5

Translation of a Macroscopic DNA Array Into a Protein Array

Biotinylated DNA was immobilized in wells of three rows on a microtiter plate, previously coated with streptavidin (50 ml of 1 nM DNA solution in TBS; row A, BRSP-48; row B, BC-UB; row C, BC-UC; total of nine wells per row). The plate was subsequently washed twice with biotin-saturated TETBS (100 ml per well) and with TBS (100 ml per well). Nine different preconjugates were prepared as described in Table 5 Each was prepared from 6 pmol of a DNA-streptavidin hybrid and 6 pmol of biotinylated anti-bovine, anti-dog or anti-mouse IgG, respectively.

TABLE 5

Preconjugates Constructed

| Sample No. | Structure |
|---|---|
| 1 | (AM) UA-STV hybrid and biotinylated anti-mouse IgG |
| 2 | (AB) UA-STV hybrid and biotinylated anti-bovine IgG |
| 3 | (AD) UA-STV hybrid and biotinylated anti-dog IgG |
| 4 | (BM) UB-STV hybrid and biotinylated anti-mouse IgG |
| 5 | (BB) UB-STV hybrid and biotinylated anti-bovine IgG |
| 6 | (BD) UB-STV hybrid and biotinylated anti-dog IgG |
| 7 | (CM) UC-STV hybrid and biotinylated anti-mouse IgG |
| 8 | (CB) UC-STV hybrid and biotinylated anti-bovine IgG |
| 9 | (CD) UC-STV hybrid and biotinylated anti-dog IgG |

All samples were subsequently diluted with RDB to a final hybrid concentration of 0.2 mM (30 ml). Three of the preconjugate solutions were combined to yield mixtures containing UA, UB and UC DNA and anti-mouse, anti-bovine or anti-dog IgGs. To test nine possible permutations, three mixtures were prepared as follows mixture A, AM+BB+CD mixture B, AB+BD+CM mixture C, AD+BM+CB Each of these mixtures was diluted with RDB to a final hybrid concentration of 40 nM and 50 ml were applied to a total of nine wells per mixture with three columns each of the three different rows, previously coated with DNA complementary to either UA, UB or UC. If the annealing of the oligonucleotides is sufficiently selective, this would result in three blocks, each with 3×3 wells, containing a different capture-antibody either against mouse, bovine or dog IgG. In parallel, a control experiment was performed with the same streptavidin-coated plate. Appropriate wells were incubated with biotinylated anti-bovine, anti-dog and anti-mouse IgG directly (50 ml of a 6.6 mg/ml solution in RDB), mimicking the expected pattern of the DNA-directed sorting. The plate was incubated for 2 hours and washed three times with TETBS (200 ml each). During capture, 50 ml of a mixture of three possible targets, bovine, dog and mouse IgGs, each at a concentration of 0.8 mg/ml in RDB, was allowed to bind to the immobilized antibody. After incubation and washing five times with TETBS (200 ml each), successful binding was determined with three different secondary antibody-alkaline phosphatase conjugates. For this purpose, each of the three conjugates was applied to one column (50 ml of a 1.3 U/ml solution in RDB) of a 3×3 block. After incubation and washing (5×200 ml TETBS; 2×200 ml TBS), the alkaline phosphatase reaction was performed and the absorbance at 405 nm was determined and recorded.

Example 6

Translation of a DNA Array into a Protein Array

Figure 5:
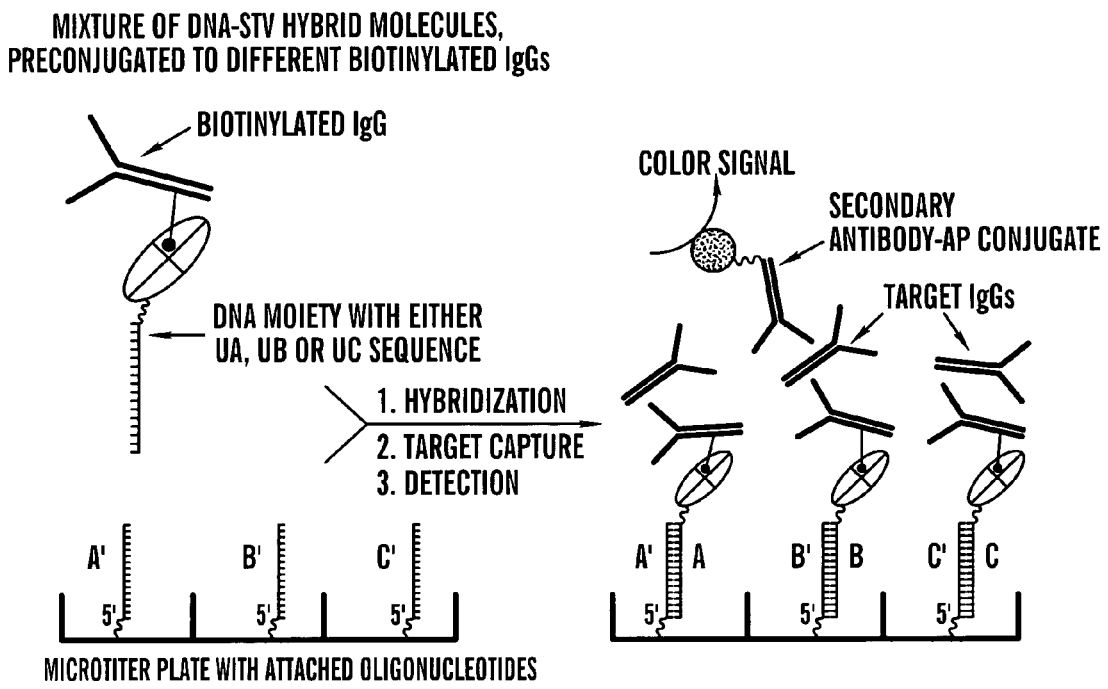
FIG. 5 Schematic representation of a translation of a DNA array into a protein chip.
Figure 6:
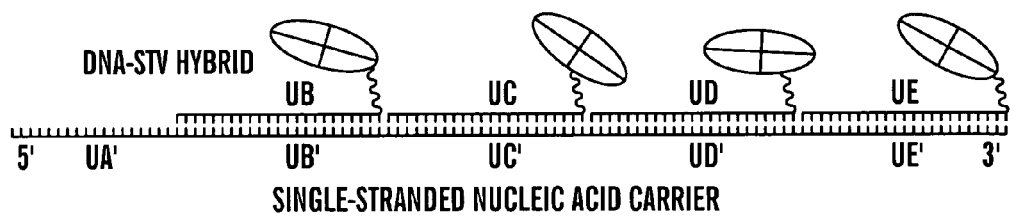
FIG. 6 Schematic representation of a supramolecular complex consisting of four DNA-STV hybrid molecules positioned alone a single-stranded nucleic acid.

A DNA chip was simulated using three different oligonucleotides immobilized in different wells of a STV-coated microtiter plate via biotin-STV interaction. This array was used for the selective immobilization of three different DNA-STV-IgG conjugates. Specific hybridization to their counterparts allowed sorting of a mixture containing three different DNA-STV hybrids, each previously conjugated to a different biotinylated rabbit antibody, with specificity against mouse, bovine or dog IgG, respectively. The translated DNA array was used to bind specifically IgG antigens from a mixture of possible IgG targets. Successful capture was determined using a commercially available AP-labeled secondary antibody. This experiment is schematically represented in FIG. 5 and the result of this sandwich ELISA is illustrated in Table 6.

spatial information for a self-assembly reaction (FIG. 6). Both single-stranded DNA and RNA were used to construct supramolecules, consisting of multiple DNA-STV hybrids as components.

A DNA carrier was prepared form a 123 bp DNA segment, generated by PCR. The plus strand contained five blocks of sequences, complementary to five synthetic 21 base oligonucleotides (UA, UB, UC, UD and UE) which were used in the preparation of hybrid molecules. This strand was also 5'-biotinylated, which allowed immobilization on STV-coated magnetic microbeads. The double-stranded DNA was denatured under alkaline conditions and the minus strand in the supernatant was removed. The immobilized carrier was used for the binding of radiolabeled DNA-STV hybrid molecules.

In separate tubes, the biotin-binding sites of purified UB-, UC-, UD- and UE-streptavidin hybrid molecules (100 pmol each in TBS) were saturated by the addition of 680 pmol of $^{14}$C-biotin (120 cpm/pmol; Amersham; Arlington Heights, Ill.) The final concentration of the hybrids was 1.2 mM. To avoid direct binding of excess biotin to the streptavidin-coated beads, 5 ml (450 pmol) streptavidin was added, sub-

TABLE 6

Absorbance Readings For the Self-Sorting Biochip ELISA

| Column No. | 1 | 2 | 3 | 4 | 5 | 6 | 7 | 8 | 9 |
|---|---|---|---|---|---|---|---|---|---|
| Secondary Ab | aM-AP | aD-AP | aB-AP | aM-AP | aD-AP | aB-AP | aM-AP | aD-AP | aB-AP |
| A-DNA | 533 | 8 | 45 | 146 | 20 | 729 | 73 | 673 | 84 |
| B-DNA | 153 | 9 | 591 | 31 | 481 | 57 | 346 | 4 | 30 |
| C-DNA | 26 | 102 | 23 | 49 | 5 | 8 | 24 | 9 | 90 |
| Control A | 177 | 17 | 15 | 50 | 7 | 279 | 20 | 334 | 28 |
| Control B | 64 | 10 | 319 | 24 | 413 | 26 | 189 | 6 | 31 |
| Control C | 35 | 941 | 75 | 186 | 5 | 19 | 61 | 0 | 265 |

Each of the six blocks contains three different capturing oligonucleotides (rows) and three different specific labels (secondary antibody—AP conjugates, columns). Each row and each column, is expected to have only one positive if the experiment is successful. In fact, in each block, one signal was dominant in each row and column. All control experiments (lower panel) show the expected results, indicating the successful capture and detection of the antigen. In some self-sorting experiments (upper panel), false or weak positives were observed in columns 4 and 9, respectively. Repetition of the experiment gave false positives again in the same positions, indicating that the hybridization step was not optimized for the particular DNA-IgG combinations. In these experiments, only two translation tests out of nine failed despite the fact that these results were obtained in a multiple sandwich assay with polyclonal antibodies. Furthermore, the melting temperatures, as well as the GC content of the oligonucleotides used, were not yet optimized for this specific application. The use of monoclonal antibodies, as well as a more careful selection of nucleic acid sequences, can improve the signal-to-background ratio.

Example 7

Assembly of a Single Linear Protein Array

The nucleic acid moieties of DNA-STV hybrids can be utilized for the construction of biological supramolecules. A single-stranded nucleic acid carrier molecule, bearing the complementary sequences, was used to provide the necessary sequently. Single kinds of either UB-, UC-, UD- or UE-streptavidin hybrids (12 pmol) or equimolar mixtures of at least two of those (12 pmol total) were added to different tubes, each containing 0.1 mg magnetic microbeads with the immobilized 123 base single-stranded DNA carrier (~1 pmol). Suspensions were diluted with RDB to a final hybrid concentration of 0.5 mM. In parallel, control samples were prepared with identical contents of hybrids but with a different, non-complementary 261 base carrier. This carrier was prepared by PCR from pUC19 template with a biotinylated primer and subsequently immobilized and denatured. Incubation of the samples was carried out for 14 hours at room temperature. Subsequently, the beads were washed seven times at 37° C. with TETBS (100 ml each) and resuspended in 50 ml TETBS and transferred to scintillation vials. Radioactivity was determined by liquid scintillation counting. Experiments with $^3$H-labeled biotin (38 cpm/pmol; Amersham; Arlington Heights, Ill.) were performed by a similar procedure.

Figure 7:
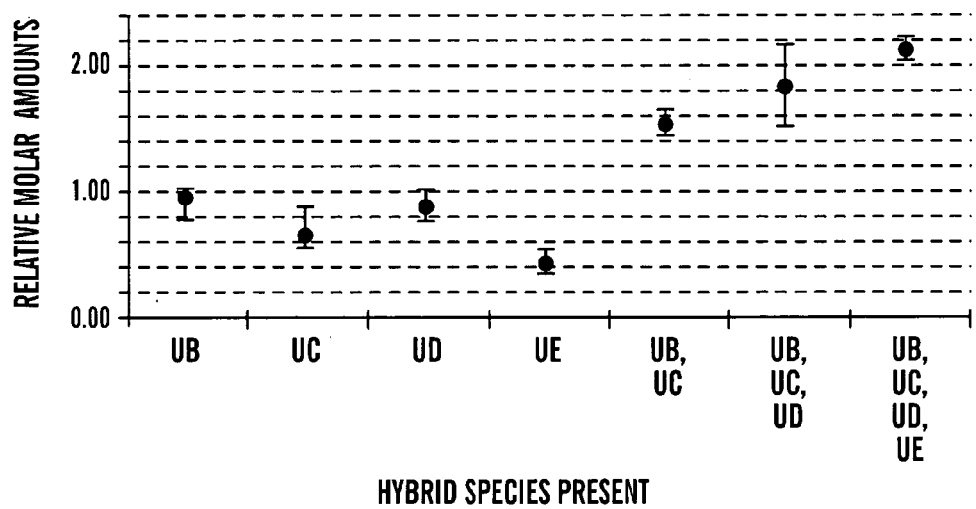
FIG. 7 Relative molar amounts of DNA-STV adducts bound to immobilized single-stranded DNA carrier.

In experiments carried out with mixtures of two or more hybrids, the identical hybrid to carrier molar ratio of ~20:1 were used, Control experiments were run in parallel with a non-complementary 261 base carrier. Radioactivity obtained from several independent experiments using either $^{14}$C- or $^3$H-labeled biotin was analyzed statistically and relative molar amounts of bound hybrid molecules were calculated (FIG. 7).

In the presence of a single adduct, the differences in the amount of each individual immobilized hybrid were sub-stoichiometric. The variations may reflect differences in the stability of the corresponding double helices, which could lead to loss of material due to extensive washing. When a mixture of different species was used, a considerable increase in immobilized material was observed. However, the data also indicated that sub-stoichiometric amounts of different hybrids bound to the carrier. This may be due to steric reasons, since the length of a 21 bp double helix is only slightly longer than the radius of a STV molecule. Therefore, a mixture of species with a different number of hybrids may have been generated. Hybrids bearing longer DNAs would determine the influence of secondary structures and possible cooperative binding effects.

Despite the greater chemical stability of single-stranded DNA, an RNA carrier has several attractive advantages. RNA-DNA duplexes are more stable than DNA-DNA duplexes. This means the use of an RNA carrier could provide greater stability to the constructs. Furthermore, RNA can be readily produced in large amounts by in vitro transcription and, if desired, can be selectively degraded by various enzymes.

Figure 8:
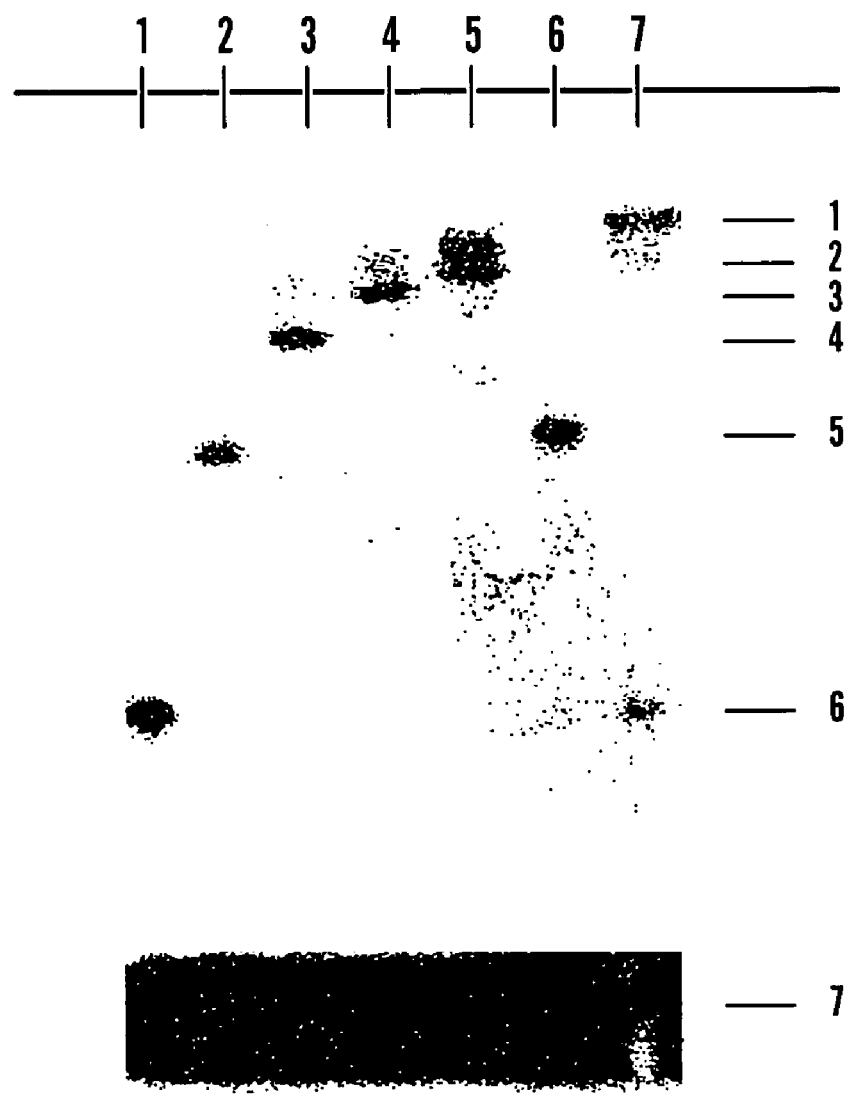
FIG. 8 Autoradiograph of a polyacrylamide gel retardation experiment using RNA as a carrier.

A transcription template containing the T7 promoter region was used to generate an RNA carrier. In gel-retardation format experiments, the RNA carrier was tested for binding of various DNA-STV hybrids which were, in some cases, pre-conjugated with biotinylated molecules such as oligonucleotides or IgGs. Briefly, radiolabeled oligonucleotide (either M13-1211 or CHP) was diluted with unlabeled oligonucleotide in TE to a final concentration of 15 mM and a specific activity of approximately 500 cpm/pmol. RNA (0.25 mM, 40 ml, 10 pmol) was mixed with 7 ml of the probe solution (98 pmol) and 7 ml RNase inhibitor (140 U; Boehringer Mannheim). The RNA-probe mixture (5 ml) was added and the solution was heated to 50° C. for one minute and allowed to cool to room temperature. For detection purposes, a $^{32}$P-labeled deoxynucleotide probe was hybridized to either the 3'- or 5'-terminal region of the carrier. The molar ratio of the components was ~50:10:1 for the radioactive probe, the proteinaceous component and the carrier, respectively. A sample buffer (2 ml) was added immediately before application to the gel. Non-denaturing PAGE was performed at 100-150 V. The gel was exposed on a PhosphorImager screen (Molecular Dynamics) overnight (14 hours) and analyzed with MD Image Quant software (Molecular Dynamics) (FIG. 8). Radiolabeled RNA (lane 1, position 6) was retarded upon addition of the complementary oligonucleotide-STV adduct (lanes 2 and 6, position 5).

Only a single band was observed in the presence of a solitary kind of hybrid, despite its 10-fold excess concentration. This indicates that non-specific hybridization between the carrier and the adduct was not significant. However, addition of DNA-STV hybrids with different nucleotide sequences caused a progressive reduction in the mobility of the product (lanes 3-6, positions 4, 3 and 2, respectively), indicating the generation of higher molecular weight species. In lane 7, a pre-formed conjugate of a DNA-STV hybrid and biotinylated anti-mouse IgG, was hybridized to the carrier molecule. The band of the hybridization product (lane 7, position 1) appeared in the same high molecular weight range and the putative four STV-containing supramolecule in lane 5. The comparable molecular masses of the two aggregates, indicated by their comparable electrophoretic behavior, identifies the presence of supramolecular bioconjugates.

Other embodiments and uses of the invention will be apparent to those skilled in the art from consideration of the specification and practice of the invention disclosed herein. All U.S. patents and other documents cited herein are specifically incorporated by reference. The specification and examples should be considered exemplary only with the tale scope and spirit of the invention indicated by the following claims.

We claim:

1. A method for forming a nucleic acid-directed immobilization array of supramolecular bioconjugates comprising the steps of:
   a) attaching a first nucleic acid to a support in a regiospecific manner;
   b) providing at least a second nucleic acid complementary to a sequence within said first nucleic acid, wherein said second nucleic acid is coupled to a bioreactive agent, wherein said second bioreactive agent is a non-nucleic acid bioreactive agent and contains a separate binding moiety that is selected to further react with a specific target;
   c) providing at least a third nucleic acid complementary to a sequence within said first or second nucleic acid, wherein said third nucleic acid is coupled to a bioreactive agent, wherein said third bioreactive agent is a non-nucleic acid bioreactive agent and contains a separate binding moiety that is selected to further react with a specific target;
   (d) hybridizing in one step said first nucleic acid to said second nucleic acid and said third nucleic acid to said first or second nucleic acid to form a supramolecular bioconjugate; and
   d) repeating steps (a)-(d) to form a plurality of immobilized supramolecular bioconjugates, wherein the separate binding moiety of each of said bioreactive agent is selected to further react with a specific target.

2. The method of claim 1, wherein the second and the third bioreactive agent in steps b) and c) further comprises a binding agent.

3. The method of claim 2, wherein the binding agent is selected from the group consisting of avidin, streptavidin, and biotin.

4. The method of claim 1, wherein the support is a ceramic, a glass, a plastic, a metal, a resin, a gel, an elastic, a wood or a combination thereof.

5. A method for assembling a supramolecular bioconjugate comprising the steps of:
   a) providing a first bioreactive complex said bioreactive complex comprising a first nucleic acid, said first nucleic acid attached to a first bioreactive agent, said first bioreactive agent comprising a first binding agent selected from the group consisting of protein A, an antibody, an Fc fragment, a Fab fragment, an antigen, a nucleic acid binding protein, and a cell adhesion molecule, wherein said first bioreactive agent is coupled to a molecule binding to said first bioreactive agent;
   b) providing at least a second bioreactive complex comprising at least two second nucleic acids, wherein one of the at least second nucleic acids serves as a first mediator nucleic acid that comprises a nucleic acid sequence that is complementary to a sequence within said first nucleic acid, said at least two second nucleic acids attached to a second bioreactive agent, said second bioreactive agent comprising a second binding agent selected from the group consisting of protein A, an antibody, an Fc fragment, a Fab fragment, an antigen, a nucleic acid binding protein, and a cell adhesion molecule, and wherein one of the at least second nucleic acids serves as a second mediator nucleic acid;
   c) providing at least a third bioreactive complex comprising at least one nucleic acid, wherein the at least one nucleic acid comprises a nucleic acid sequence that is complementary to at least portion of the second mediator nucleic acid attached to the second bioreactive complex; and
   d) hybridizing in one step said complementary nucleic acids of said second and third bioreactive complex to said first and second nucleic acid of said first and second bioreactive complex to form a supramolecular bioconjugate, wherein at least one of the second or the third bioreactive agent, is selected to further react with a bioreactive target, while part of the supramolecular bioconjugate.

6. The method of claim 5 wherein said first nucleic acid is between about 10 to about 1000 nucleotides in length.

7. The method of claim 5 wherein said second nucleic acid is between about 10 to about 1000 nucleotides in length.

8. A supramolecular bioconjugate assembled by the method of claim 5.

9. A plurality of supramolecular bioconjugates formed by the method of claim 5.

10. The method of claim 5, wherein said first nucleic acid and said second nucleic acid are DNA, RNA or PNA.

11. The method of claim 5, wherein the second nucleic acid is between 10 to 600 nucleotides in length.

12. A method for forming a plurality of immobilized supramolecular bioconjugates comprising the steps of:
  a) attaching to a support in a regiospecific manner a first bioreactive complex wherein said first bioreactive complex comprises a first nucleic acid wherein said first nucleic acid is attached to a first bioreactive agent, said first bioreactive agent comprising a first binding agent selected from the group consisting of avidin, streptavidin, biotin, protein A, an antibody, an Fc fragment, a Fab fragment, an antigen, a nucleic acid binding protein, and a cell adhesion molecule and coupling said first bioreactive agent to a molecule capable of binding to said first binding agent;
  b) providing at least a second bioreactive complex said second bioreactive complex comprising a second nucleic acid complementary to a sequence within said first nucleic acid, said second nucleic acid attached to a second bioreactive agent, said second bioreactive agent comprising a second binding agent selected from the group consisting of avidin, streptavidin, biotin, protein A, an antibody, an Fc fragment, a Fab fragment, an antigen, a nucleic acid binding protein, and a cell adhesion molecule, and further comprising a third nucleic acid;
  c) providing at least a third bioreactive complex said third bioreactive complex comprising a fourth nucleic acid complementary to a sequence within said third nucleic acid, said fourth nucleic acid attached to a third bioreactive agent, said third bioreactive agent comprising a third binding agent selected from the group consisting of avidin, streptavidin, biotin, protein A, an antibody, an Fc fragment, a Fab fragment, an antigen, a nucleic acid binding protein, and a cell adhesion molecule;
  d) hybridizing, in one step said first nucleic acid to said second nucleic acid and said third nucleic acid to said fourth nucleic acid to form a supramolecular bioconjugate; and
  e) repeating steps (a)-(d) to form a plurality of immobilized supramolecular bioconjugates, wherein the second bioreactive agent is selected to react further with a specific bioreactive target while part of the supramolecular bioconjugates.

13. A method for assembling a supramolecular bioconjugate comprising the steps of:
  a) providing a first bioreactive complex said bioreactive complex comprising a first nucleic acid, said first nucleic acid attached to a first bioreactive agent, said first bioreactive agent comprising a first binding agent selected from the group consisting of protein A, an antibody, an Fc fragment, a Fab fragment, an antigen, a nucleic acid binding protein, and a cell adhesion molecule, wherein said first bioreactive agent is coupled to a molecule binding to said first bioreactive agent;
  b) providing at least a second bioreactive complex comprising a second nucleic acid, wherein the at least second nucleic acid comprises a nucleic acid sequence that is complementary to a portion of the sequence within said first nucleic acid, said second nucleic acid attached to a second bioreactive agent, said second bioreactive agent comprising a second binding agent selected from the group consisting of protein A, an antibody, an Fc fragment, a Fab fragment, an antigen, a nucleic acid binding protein, and a cell adhesion molecule;
  c) providing at least a third bioreactive complex comprising a third nucleic acid, wherein the third nucleic acid comprises a nucleic acid sequence that is complementary to at least portion of the first nucleic acid ; and
  d) in one step hybridizing said complementary nucleic acids in said at least the second and the third bioreactive complex to said first nucleic acid of said first bioreactive complex to form a supramolecular bioconjugate, wherein at least one of the second or the third bioreactive agent will further react with an intended bioreactive target, while part of the supramolecular bioconjugate.

14. The method of claim 12 or 13, wherein the plurality of immobilized supramolecular bioconjugates comprises at least 10 immobilized supramolecular bioconjugates.

15. The method of claim 12 or 13, wherein the plurality of immobilized supramolecular bioconjugates comprises at least 1,000 immobilized supramolecular bioconjugates.

16. The method of claim 12 or 13, wherein the plurality of immobilized supramolecular bioconjugates comprises at least 100,000 immobilized supramolecular bioconjugates.

17. The method of claim 12 or 13, wherein the plurality of immobilized supramolecular bioconjugates comprises at least 1,000,000 immobilized supramolecular bioconjugates.

18. The method of claim 12 or 13, wherein the first, the second and the third binding agent is selected from the group consisting of avidin, streptavidin, and biotin.

19. A method for forming a nucleic acid-directed immobilization array of supramolecular bioconjugates comprising the steps of:
  a) attaching a first nucleic acid to a support in a regiospecific manner;
  b) providing at least a second nucleic acid complementary to a sequence within said first nucleic acid, wherein said second nucleic acid is coupled to a bioreactive agent, wherein said second bioreactive agent is a non-nucleic acid bioreactive agent and contains a separate binding moiety that is selected to further react with a specific target;
  c) providing at least a third nucleic acid complementary to a sequence within said first or second nucleic acid, wherein said third nucleic acid is coupled to a bioreactive agent, wherein said third bioreactive agent is a non-nucleic acid bioreactive agent and contains a separate binding moiety that is selected to further react with a specific target;
  (d) hybridizing in one step said first nucleic acid to said second nucleic acid and said third nucleic acid to said first or second nucleic acid to form a supramolecular bioconjugate; and
  d) repeating steps (a)-(d) to form a plurality of immobilized supramolecular bioconjugates, wherein the separate binding moiety of each of said bioreactive agent is selected to further react with a specific target.

20. The method of claim 12 or 19, wherein the support is a ceramic, a glass, a plastic, a metal, a resin, a gel, an elastic, a wood or a combination thereof.

* * * * *

UNITED STATES PATENT AND TRADEMARK OFFICE
CERTIFICATE OF CORRECTION

PATENT NO. : 7,569,341 B2
APPLICATION NO. : 08/967269
DATED : August 4, 2009
INVENTOR(S) : Christof M. Niemeyer It is certified that error appears in the above-identified patent and that said Letters Patent is hereby corrected as shown below:

"barrels" at col. 2, line 43 should be "barriers" as shown in specification as filed pg. 2, line 30.
"Cirrafornia" at Table 1, col. 2 should be italicized as shown in specification as filed pg. 2, line 8.
"For" at col. 3, line 35 should be "for" as shown in specification as filed pg. 4, line 5.
"bacteriostaitic" at col. 4, lines 39-40 should be "bacteriostatic" as shown in specification as filed pg. 5, line 28.
Paragraph at col. 6, line 24 should be part of paragraph starting at col. 6, line 21 as shown in specification as filed pg. 8, line 21.
"he" at col. 8, line 45 should be "be" as shown in specification as filed pg. 12, line 8.
";" at col. 12, line 17 should be removed as shown in specification as filed pg. 17, line 26.
"mid" at col. 15, line 34 should be "and" as shown in specification as filed pg. 22, line 29.
"in viva" at col. 16, line 7 should be "*in vivo*" as shown in specification as filed pg. 23, line 27.
"constricts" at col. 16, line 49 should be "constructs" as shown in specification as filed pg. 24, line 26.
"useful Compositions" at col. 16, line 59 should be "useful. Compositions" as shown in specification as filed pg. 25, lines 2-3.
"37° C." at col. 18, line 46; col. 20, line 65; col. 23, line 6; col. 26, line 51; col. 27, line 34 should be "37° C" as shown in specification as filed pg. 27, line 15; pg. 30, line 13; pg. 33, line 13; pg. 38, line 15; pg. 39, line 18.
"TAA TAC GAC TCA CTA TAG" at Table 3, line 6 should be "<u>TAA TAC GAC TCA CTA TAG</u>" as shown in specification as filed pg. 28, line 5.
"(MESTBS) The" at col. 19, line 53 should be "(MESTBS). The" as shown in specification as filed pg. 29, line 2.
"TF-10" at col. 20, line 22 should be "TE-10" as shown in specification as filed pg. 29, line 16.
"STY" at col. 21, line 46 should be "STV" as shown in specification as filed pg. 31, line 14.
"0.2mM, Aliquots" at col. 23, line 39 should be "0.2mM. Aliquots" as shown in specification as filed pg. 34, line 7.
Paragraph at col. 23, line 61 should be part of paragraph starting at col. 23, line 31 as shown in specification as filed pg. 34, line 22.
"5 Each" at col. 24, line 17 should be "5. Each" as shown in specification as filed pg. 35, lines 6-7.
In Table 6, the following numbers should be bold: col. 1 - 533, 177; col. 2 - 102, 941; col. 3 - 591, 319; col. 4 - 49, 186; col. 5 - 481, 413; col. 6 - 729, 279; col. 7 - 346, 189; col. 8 - 673, 334; col. 9 - 90, 265; as shown in specification as filed pg. 36, lines 30-35.

"tale" at col. 28, line 34 should be "time" as shown in specification as filed pg. 40, line 12.

"in vivo" and "in vitro" need to be italicized at col. 3, lines 1 and 4 (as shown in specification pg. 3, lines 10 and 13); col. 6, lines 8, 9,11, and 12 (as shown in specification pg. 8, lines 10, 12, and 13); col. 7, lines 1 and 2 (as shown in specification pg. 9, line 12); col. 8, line 17 (as shown in specification pg. 11, line 20); col. 14, lines 29, 55 and 56 (as shown in specification pg. 21, lines 8 and 28); col. 15, line 24 (as shown in specification pg. 22, line 22); col. 19, line 66 (as shown in specification pg. 29, line 12); col. 20, line 18 (as shown in specification pg. 29, lines 14).

Signed and Sealed this

Fifth Day of January, 2010

David J. Kappos
*Director of the United States Patent and Trademark Office*

SEQUENCE LISTING (1) GENERAL INFORMATION:

(iii) NUMBER OF SEQUENCES: 16

(2) INFORMATION FOR SEQ ID NO:1:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (xi) SEQUENCE DESCRIPTION: SEQ ID NO:1:

TCCTGTGTGA AATTGTTATC CGCT                                           24

(2) INFORMATION FOR SEQ ID NO:2:

(i) SEQUENCE CHARACTERISTICS:
       (A) LENGTH: 24 base pairs
       (B) TYPE: nucleic acid
       (C) STRANDEDNESS: single
       (D) TOPOLOGY: linear (xi) SEQUENCE DESCRIPTION: SEQ ID NO:2:

AGCGGATAAC AATTTCACAC AGGA                                           24

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:3:

GTAATCATGG TCATAGCTGT T                                              21

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:4:

ACCAGCTATG ACCATGATTA C                                              21

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:5:

AACAGCTATG ACCTCGAATA C                                              21

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:6:

CCGGGTACCG AGCTCGAATT C                                              21

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:7:

GAATTCGAGC TCGGTACCCG G                                              21

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:8:

GAATTCGAGC TCGGTACCCG G                                              21

(2) INFORMATION FOR SEQ ID NO:9:

```
    (i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:9:

CAGGTCGACT CTAGAGGATC C                                             21

(2) INFORMATION FOR SEQ ID NO:10:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (xi) SEQUENCE DESCRIPTION: SEQ ID NO:10:

CAGCTCGACT CTAGAGGATC CAGTGCCAAD CT                                 32

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:11:

AGTGCCAAGC TTGCATGCCT G                                             21

(2) INFORMATION FOR SEQ ID NO:12:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:12:

AGCGGATAAC AATTTCACAC AGGA                                          24

(2) INFORMATION FOR SEQ ID NO:13:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:13:

GTAAAACGAC GCCCAGT                                                  17

(2) INFORMATION FOR SEQ ID NO:14:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:14:

TCCTAATACG ACTCACTATA GCGGATAACA ATTTCACACA G                       41

(2) INFORMATION FOR SEQ ID NO:15:
```

-continued (i) SEQUENCE CHARACTERISTICS:
    (A) LENGTH: 18 base pairs
    (B) TYPE: nucleic acid
    (C) STRANDEDNESS: single
    (D) TOPOLOGY: linear (xi) SEQUENCE DESCRIPTION: SEQ ID NO:15:

GCGGATAACA ATTTCACA                                                    18

(2) INFORMATION FOR SEQ ID NO:16:

(i) SEQUENCE CHARACTERISTICS:
    (A) LENGTH: 18 base pairs
    (B) TYPE: nucleic acid
    (C) STRANDEDNESS: single
    (D) TOPOLOGY: linear (xi) SEQUENCE DESCRIPTION: SEQ ID NO:16:

TGTGAAATTG TTATCCGC                                                    18